(12) United States Patent
Jung et al.

(10) Patent No.: US 7,968,316 B2
(45) Date of Patent: Jun. 28, 2011

(54) METHOD FOR THE MASS PRODUCTION OF IMMUNOGLOBULIN FC REGION DELETED INITIAL METHIONINE RESIDUES

(75) Inventors: Sung youb Jung, Yongin-si (KR); Jin Sun Kim, Gwangmyeong-si (KR); Jin hwan Shin, Seoul (KR); Se-Chang Kwon, Seoul (KR); Gwan-Sun Lee, Seoul (KR); Dae hae Song, Seoul (KR)

(73) Assignee: Hanmi Holdings Co., Ltd., Seoul (KR)

( * ) Notice: Subject to any disclaimer, the term of this patent is extended or adjusted under 35 U.S.C. 154(b) by 157 days.

(21) Appl. No.: 12/063,379

(22) PCT Filed: Aug. 16, 2006

(86) PCT No.: PCT/KR2006/003207
§ 371 (c)(1),
(2), (4) Date: Jun. 17, 2008

(87) PCT Pub. No.: WO2007/021129
PCT Pub. Date: Feb. 22, 2007

(65) Prior Publication Data
US 2008/0293106 A1    Nov. 27, 2008

(30) Foreign Application Priority Data
Aug. 16, 2005 (KR) ................. 10-2005-0074989

(51) Int. Cl.
C12P 21/04 (2006.01)
C12N 15/64 (2006.01)
C12N 15/00 (2006.01)
C07H 21/04 (2006.01)

(52) U.S. Cl. .............. 435/69.6; 435/91.4; 435/320.1; 536/23.53

(58) Field of Classification Search .............. None
See application file for complete search history.

(56) References Cited

U.S. PATENT DOCUMENTS

| | | | |
|---|---|---|---|
| 5,349,053 A | 9/1994 | Landolfi | |
| 5,585,097 A | 12/1996 | Bolt et al. | |
| 5,605,690 A | 2/1997 | Jacobs et al. | |
| 5,723,125 A | 3/1998 | Chang et al. | |
| 5,908,626 A | 6/1999 | Chang et al. | |
| 6,030,613 A | 2/2000 | Blumberg et al. | |
| 6,165,476 A * | 12/2000 | Strom et al. | 424/195.11 |
| 6,660,843 B1 | 12/2003 | Feige et al. | |
| 2001/0053539 A1 | 12/2001 | Lauffer et al. | |
| 2003/0073164 A1 | 4/2003 | Simmons et al. | |
| 2003/0082679 A1 | 5/2003 | Sun et al. | |
| 2004/0044188 A1 | 3/2004 | Feige et al. | |
| 2004/0053845 A1 | 3/2004 | Feige et al. | |
| 2004/0175824 A1* | 9/2004 | Sun et al. | 435/326 |
| 2006/0276633 A1* | 12/2006 | Jung et al. | 530/387.1 |

FOREIGN PATENT DOCUMENTS

| | | |
|---|---|---|
| EP | 0 227 110 | 12/1986 |
| EP | 0 227 110 A3 | 8/1988 |
| KR | 1020050047033 A | 5/2005 |
| WO | WO 99/02709 A1 | 1/1999 |
| WO | WO 01/03737 A1 | 1/2001 |
| WO | 01/18203 A1 | 3/2001 |
| WO | 2005/047334 A1 | 5/2005 |

OTHER PUBLICATIONS

Sheridan J.M. et al. 'Solid-phase synthesis and cyclization of a large branched peptide from LgG Fc with affinity for Fc gammaRI' J pept Sci., Dec. 1999, vol. 5, No. 12, pp. 555-562.

Kim, J.K. et al. 'Localization of the site of the murine IgG1 molecule that is involved in binding to the murine intestinal Fc receptor' Eur J Immunol., Oct. 1994, vol. 24, No. 10, pp. 2429-2434.

European Search Report issued in EP 06783620, mailed Feb. 23, 2010.

* cited by examiner

*Primary Examiner* — Anne M. Gussow
(74) *Attorney, Agent, or Firm* — Sughrue Mion, PLLC

(57) ABSTRACT

Disclosed is a method for the mass production of a monomeric or dimeric immunoglobulin Fc region, free of initial methionine residues, using a recombinant expression vector comprising a nucleotide sequence coding for a recombinant immunoglobulin Fc region comprising an immunoglobulin Fc region linked at the N-terminus thereof to an immunoglobulin Fc region via a peptide bond.

15 Claims, 5 Drawing Sheets

SEQUENCE LISTING

<160> NUMBER OF SEQ ID NOS: 87

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gggcatatgt catgcccagc acctgagttc ctggggga                39

<210> SEQ ID NO 2
<211> LENGTH: 32
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 2
gggggatccc tatttaccca gagacaggga ga                                      32

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggcatatgc catcatgccc agcacctgag ttcctgggg                               39

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggcatatgt gcccatcatg cccagcacct gagttcctgg                              40

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggcatatgt gcccagcacc tgagttcctg ggggga                                  36

<210> SEQ ID NO 6
<211> LENGTH: 663
<212> TYPE: DNA
<213> ORGANISM: Homo sapiens
<220> FEATURE:
<221> NAME/KEY: CDS
<222> LOCATION: (1)..(663)

<400> SEQUENCE: 6 atg tca tgc cca gca cct gag ttc ctg ggg gga cca tca gtc ttc ctg          48
Met Ser Cys Pro Ala Pro Glu Phe Leu Gly Gly Pro Ser Val Phe Leu
1               5                   10                  15 ttc ccc cca aaa ccc aag gac act ctc atg atc tcc cgg acc cct gag          96
Phe Pro Pro Lys Pro Lys Asp Thr Leu Met Ile Ser Arg Thr Pro Glu
            20                  25                  30 gtc acg tgc gtg gtg gtg gac gtg agc cag gaa gac ccc gag gtc cag         144
Val Thr Cys Val Val Val Asp Val Ser Gln Glu Asp Pro Glu Val Gln
        35                  40                  45 ttc aac tgg tac gtg gat ggc gtg gag gtg cat aat gcc aag aca aag         192
Phe Asn Trp Tyr Val Asp Gly Val Glu Val His Asn Ala Lys Thr Lys
    50                  55                  60 ccg cgg gag gag cag ttc aac agc acg tac cgt gtg gtc agc gtc ctc         240
Pro Arg Glu Glu Gln Phe Asn Ser Thr Tyr Arg Val Val Ser Val Leu
65                  70                  75                  80 acc gtc ctg cac cag gac tgg ctg aac ggc aag gag tac aag tgc aag         288
Thr Val Leu His Gln Asp Trp Leu Asn Gly Lys Glu Tyr Lys Cys Lys
```

```
gtc tcc aac aaa ggc ctc ccg tcc tcc atc gag aaa acc atc tcc aaa      336
Val Ser Asn Lys Gly Leu Pro Ser Ser Ile Glu Lys Thr Ile Ser Lys
        100                 105                 110 gcc aaa ggg cag ccc cga gag cca cag gtg tac acc ctg ccc cca tcc      384
Ala Lys Gly Gln Pro Arg Glu Pro Gln Val Tyr Thr Leu Pro Pro Ser
        115                 120                 125 cag gag gag atg acc aag aac cag gtc agc ctg acc tgc ctg gtc aaa      432
Gln Glu Glu Met Thr Lys Asn Gln Val Ser Leu Thr Cys Leu Val Lys
        130                 135                 140 ggc ttc tac ccc agc gac atc gcc gtg gag tgg gag agc aat ggg cag      480
Gly Phe Tyr Pro Ser Asp Ile Ala Val Glu Trp Glu Ser Asn Gly Gln
145                 150                 155                 160 ccg gag aac aac tac aag acc acg cct ccc gtg ctg gac tcc gac ggc      528
Pro Glu Asn Asn Tyr Lys Thr Thr Pro Pro Val Leu Asp Ser Asp Gly
                165                 170                 175 tcc ttc ttc ctc tac agc agg cta acc gtg gac aag agc agg tgg cag      576
Ser Phe Phe Leu Tyr Ser Arg Leu Thr Val Asp Lys Ser Arg Trp Gln
        180                 185                 190 gag ggg aat gtc ttc tca tgc tcc gtg atg cat gag gct ctg cac aac      624
Glu Gly Asn Val Phe Ser Cys Ser Val Met His Glu Ala Leu His Asn
        195                 200                 205 cac tac aca cag aag agc ctc tcc ctg tct ctg ggt aaa                  663
His Tyr Thr Gln Lys Ser Leu Ser Leu Ser Leu Gly Lys
        210                 215                 220

<210> SEQ ID NO 7
<211> LENGTH: 221
<212> TYPE: PRT
<213> ORGANISM: Homo sapiens

<400> SEQUENCE: 7

Met Ser Cys Pro Ala Pro Glu Phe Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Asp Val Ser Gln Glu Asp Pro Glu Val Gln
        35                  40                  45

Phe Asn Trp Tyr Val Asp Gly Val Glu Val His Asn Ala Lys Thr Lys
    50                  55                  60

Pro Arg Glu Glu Gln Phe Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Gly Leu Pro Ser Ser Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Gln Glu Glu Met Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Arg Leu Thr Val Asp Lys Ser Arg Trp Gln
            180                 185                 190

Glu Gly Asn Val Phe Ser Cys Ser Val Met His Glu Ala Leu His Asn
        195                 200                 205
```

```
His Tyr Thr Gln Lys Ser Leu Ser Leu Ser Leu Gly Lys
    210                 215                 220

<210> SEQ ID NO 8
<211> LENGTH: 666
<212> TYPE: DNA
<213> ORGANISM: Homo sapiens
<220> FEATURE:
<221> NAME/KEY: CDS
<222> LOCATION: (1)..(666)

<400> SEQUENCE: 8 atg cca tca tgc cca gca cct gag ttc ctg ggg gga cca tca gtc ttc       48
Met Pro Ser Cys Pro Ala Pro Glu Phe Leu Gly Gly Pro Ser Val Phe
1               5                   10                  15 ctg ttc ccc cca aaa ccc aag gac act ctc atg atc tcc cgg acc cct       96
Leu Phe Pro Pro Lys Pro Lys Asp Thr Leu Met Ile Ser Arg Thr Pro
            20                  25                  30 gag gtc acg tgc gtg gtg gtg gac gtg agc cag gaa gac ccc gag gtc      144
Glu Val Thr Cys Val Val Val Asp Val Ser Gln Glu Asp Pro Glu Val
        35                  40                  45 cag ttc aac tgg tac gtg gat ggc gtg gag gtg cat aat gcc aag aca      192
Gln Phe Asn Trp Tyr Val Asp Gly Val Glu Val His Asn Ala Lys Thr
    50                  55                  60 aag ccg cgg gag gag cag ttc aac agc acg tac cgt gtg gtc agc gtc      240
Lys Pro Arg Glu Glu Gln Phe Asn Ser Thr Tyr Arg Val Val Ser Val
65                  70                  75                  80 ctc acc gtc ctg cac cag gac tgg ctg aac ggc aag gag tac aag tgc      288
Leu Thr Val Leu His Gln Asp Trp Leu Asn Gly Lys Glu Tyr Lys Cys
                85                  90                  95 aag gtc tcc aac aaa ggc ctc ccg tcc tcc atc gag aaa acc atc tcc      336
Lys Val Ser Asn Lys Gly Leu Pro Ser Ser Ile Glu Lys Thr Ile Ser
            100                 105                 110 aaa gcc aaa ggg cag ccc cga gag cca cag gtg tac acc ctg ccc cca      384
Lys Ala Lys Gly Gln Pro Arg Glu Pro Gln Val Tyr Thr Leu Pro Pro
        115                 120                 125 tcc cag gag gag atg acc aag aac cag gtc agc ctg acc tgc ctg gtc      432
Ser Gln Glu Glu Met Thr Lys Asn Gln Val Ser Leu Thr Cys Leu Val
    130                 135                 140 aaa ggc ttc tac ccc agc gac atc gcc gtg gag tgg gag agc aat ggg      480
Lys Gly Phe Tyr Pro Ser Asp Ile Ala Val Glu Trp Glu Ser Asn Gly
145                 150                 155                 160 cag ccg gag aac aac tac aag acc acg cct ccc gtg ctg gac tcc gac      528
Gln Pro Glu Asn Asn Tyr Lys Thr Thr Pro Pro Val Leu Asp Ser Asp
                165                 170                 175 ggc tcc ttc ttc ctc tac agc agg cta acc gtg gac aag agc agg tgg      576
Gly Ser Phe Phe Leu Tyr Ser Arg Leu Thr Val Asp Lys Ser Arg Trp
            180                 185                 190 cag gag ggg aat gtc ttc tca tgc tcc gtg atg cat gag gct ctg cac      624
Gln Glu Gly Asn Val Phe Ser Cys Ser Val Met His Glu Ala Leu His
        195                 200                 205 aac cac tac aca cag aag agc ctc tcc ctg tct ctg ggt aaa              666
Asn His Tyr Thr Gln Lys Ser Leu Ser Leu Ser Leu Gly Lys
    210                 215                 220

<210> SEQ ID NO 9
<211> LENGTH: 222
<212> TYPE: PRT
<213> ORGANISM: Homo sapiens

<400> SEQUENCE: 9

Met Pro Ser Cys Pro Ala Pro Glu Phe Leu Gly Gly Pro Ser Val Phe
```

```
                  1               5                  10                 15
            Leu Phe Pro Pro Lys Pro Lys Asp Thr Leu Met Ile Ser Arg Thr Pro
                              20                  25                  30

Glu Val Thr Cys Val Val Val Asp Val Ser Gln Glu Asp Pro Glu Val
                          35                  40                  45

Gln Phe Asn Trp Tyr Val Asp Gly Val Glu Val His Asn Ala Lys Thr
                      50                  55                  60

Lys Pro Arg Glu Glu Gln Phe Asn Ser Thr Tyr Arg Val Val Ser Val
             65                  70                  75                  80

Leu Thr Val Leu His Gln Asp Trp Leu Asn Gly Lys Glu Tyr Lys Cys
                              85                  90                  95

Lys Val Ser Asn Lys Gly Leu Pro Ser Ser Ile Glu Lys Thr Ile Ser
                          100                 105                 110

Lys Ala Lys Gly Gln Pro Arg Glu Pro Gln Val Tyr Thr Leu Pro Pro
                      115                 120                 125

Ser Gln Glu Glu Met Thr Lys Asn Gln Val Ser Leu Thr Cys Leu Val
                      130                 135                 140

Lys Gly Phe Tyr Pro Ser Asp Ile Ala Val Glu Trp Glu Ser Asn Gly
            145                 150                 155                 160

Gln Pro Glu Asn Asn Tyr Lys Thr Thr Pro Pro Val Leu Asp Ser Asp
                              165                 170                 175

Gly Ser Phe Phe Leu Tyr Ser Arg Leu Thr Val Asp Lys Ser Arg Trp
                          180                 185                 190

Gln Glu Gly Asn Val Phe Ser Cys Ser Val Met His Glu Ala Leu His
                      195                 200                 205

Asn His Tyr Thr Gln Lys Ser Leu Ser Leu Ser Leu Gly Lys
                      210                 215                 220

<210> SEQ ID NO 10
<211> LENGTH: 669
<212> TYPE: DNA
<213> ORGANISM: Homo sapiens
<220> FEATURE:
<221> NAME/KEY: CDS
<222> LOCATION: (1)..(669)

<400> SEQUENCE: 10 atg tgc cca tca tgc cca gca cct gag ttc ctg ggg gga cca tca gtc    48
Met Cys Pro Ser Cys Pro Ala Pro Glu Phe Leu Gly Gly Pro Ser Val
 1               5                  10                  15 ttc ctg ttc ccc cca aaa ccc aag gac act ctc atg atc tcc cgg acc    96
Phe Leu Phe Pro Pro Lys Pro Lys Asp Thr Leu Met Ile Ser Arg Thr
                 20                  25                  30 cct gag gtc acg tgc gtg gtg gtg gac gtg agc cag gaa gac ccc gag    144
Pro Glu Val Thr Cys Val Val Val Asp Val Ser Gln Glu Asp Pro Glu
             35                  40                  45 gtc cag ttc aac tgg tac gtg gat ggc gtg gag gtg cat aat gcc aag    192
Val Gln Phe Asn Trp Tyr Val Asp Gly Val Glu Val His Asn Ala Lys
         50                  55                  60 aca aag ccg cgg gag gag cag ttc aac agc acg tac cgt gtg gtc agc    240
Thr Lys Pro Arg Glu Glu Gln Phe Asn Ser Thr Tyr Arg Val Val Ser
 65                  70                  75                  80 gtc ctc acc gtc ctg cac cag gac tgg ctg aac ggc aag gag tac aag    288
Val Leu Thr Val Leu His Gln Asp Trp Leu Asn Gly Lys Glu Tyr Lys
                 85                  90                  95 tgc aag gtc tcc aac aaa ggc ctc ccg tcc tcc atc gag aaa acc atc    336
Cys Lys Val Ser Asn Lys Gly Leu Pro Ser Ser Ile Glu Lys Thr Ile
            100                 105                 110
```

```
tcc aaa gcc aaa ggg cag ccc cga gag cca cag gtg tac acc ctg ccc      384
Ser Lys Ala Lys Gly Gln Pro Arg Glu Pro Gln Val Tyr Thr Leu Pro
        115                 120                 125 cca tcc cag gag gag atg acc aag aac cag gtc agc ctg acc tgc ctg      432
Pro Ser Gln Glu Glu Met Thr Lys Asn Gln Val Ser Leu Thr Cys Leu
130                 135                 140 gtc aaa ggc ttc tac ccc agc gac atc gcc gtg gag tgg gag agc aat      480
Val Lys Gly Phe Tyr Pro Ser Asp Ile Ala Val Glu Trp Glu Ser Asn
145                 150                 155                 160 ggg cag ccg gag aac aac tac aag acc acg cct ccc gtg ctg gac tcc      528
Gly Gln Pro Glu Asn Asn Tyr Lys Thr Thr Pro Pro Val Leu Asp Ser
                165                 170                 175 gac ggc tcc ttc ttc ctc tac agc agg cta acc gtg gac aag agc agg      576
Asp Gly Ser Phe Phe Leu Tyr Ser Arg Leu Thr Val Asp Lys Ser Arg
            180                 185                 190 tgg cag gag ggg aat gtc ttc tca tgc tcc gtg atg cat gag gct ctg      624
Trp Gln Glu Gly Asn Val Phe Ser Cys Ser Val Met His Glu Ala Leu
        195                 200                 205 cac aac cac tac aca cag aag agc ctc tcc ctg tct ctg ggt aaa          669
His Asn His Tyr Thr Gln Lys Ser Leu Ser Leu Ser Leu Gly Lys
    210                 215                 220
```

<210> SEQ ID NO 11
<211> LENGTH: 223
<212> TYPE: PRT
<213> ORGANISM: Homo sapiens

<400> SEQUENCE: 11

```
Met Cys Pro Ser Cys Pro Ala Pro Glu Phe Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Arg Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Ser Leu Gly Lys
    210                 215                 220
```

<210> SEQ ID NO 12

```
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 12 atg tgc cca gca cct gag ttc ctg ggg gga cca tca gtc ttc ctg ttc      48
Met Cys Pro Ala Pro Glu Phe Leu Gly Gly Pro Ser Val Phe Leu Phe
 1               5                  10                  15 ccc cca aaa ccc aag gac act ctc atg atc tcc cgg acc cct gag gtc      96
Pro Pro Lys Pro Lys Asp Thr Leu Met Ile Ser Arg Thr Pro Glu Val
             20                  25                  30 acg tgc gtg gtg gtg gac gtg agc cag gaa gac ccc gag gtc cag ttc     144
Thr Cys Val Val Val Asp Val Ser Gln Glu Asp Pro Glu Val Gln Phe
         35                  40                  45 aac tgg tac gtg gat ggc gtg gag gtg cat aat gcc aag aca aag ccg     192
Asn Trp Tyr Val Asp Gly Val Glu Val His Asn Ala Lys Thr Lys Pro
     50                  55                  60 cgg gag gag cag ttc aac agc acg tac cgt gtg gtc agc gtc ctc acc     240
Arg Glu Glu Gln Phe Asn Ser Thr Tyr Arg Val Val Ser Val Leu Thr
 65                  70                  75                  80 gtc ctg cac cag gac tgg ctg aac ggc aag gag tac aag tgc aag gtc     288
Val Leu His Gln Asp Trp Leu Asn Gly Lys Glu Tyr Lys Cys Lys Val
                 85                  90                  95 tcc aac aaa ggc ctc ccg tcc tcc atc gag aaa acc atc tcc aaa gcc     336
Ser Asn Lys Gly Leu Pro Ser Ser Ile Glu Lys Thr Ile Ser Lys Ala
            100                 105                 110 aaa ggg cag ccc cga gag cca cag gtg tac acc ctg ccc cca tcc cag     384
Lys Gly Gln Pro Arg Glu Pro Gln Val Tyr Thr Leu Pro Pro Ser Gln
        115                 120                 125 gag gag atg acc aag aac cag gtc agc ctg acc tgc ctg gtc aaa ggc     432
Glu Glu Met Thr Lys Asn Gln Val Ser Leu Thr Cys Leu Val Lys Gly
    130                 135                 140 ttc tac ccc agc gac atc gcc gtg gag tgg gag agc aat ggg cag ccg     480
Phe Tyr Pro Ser Asp Ile Ala Val Glu Trp Glu Ser Asn Gly Gln Pro
145                 150                 155                 160 gag aac aac tac aag acc acg cct ccc gtg ctg gac tcc gac ggc tcc     528
Glu Asn Asn Tyr Lys Thr Thr Pro Pro Val Leu Asp Ser Asp Gly Ser
                165                 170                 175 ttc ttc ctc tac agc agg cta acc gtg gac aag agc agg tgg cag gag     576
Phe Phe Leu Tyr Ser Arg Leu Thr Val Asp Lys Ser Arg Trp Gln Glu
            180                 185                 190 ggg aat gtc ttc tca tgc tcc gtg atg cat gag gct ctg cac aac cac     624
Gly Asn Val Phe Ser Cys Ser Val Met His Glu Ala Leu His Asn His
        195                 200                 205 tac aca cag aag agc ctc tcc ctg tct ctg ggt aaa                     660
Tyr Thr Gln Lys Ser Leu Ser Leu Ser Leu Gly Lys
    210                 215                 220

<210> SEQ ID NO 13
<211> LENGTH: 220
<212> TYPE: PRT
<213> ORGANISM: Homo sapiens

<400> SEQUENCE: 13

Met Cys Pro Ala Pro Glu Phe Leu Gly Gly Pro Ser Val Phe Leu Phe
 1               5                  10                  15

Pro Pro Lys Pro Lys Asp Thr Leu Met Ile Ser Arg Thr Pro Glu Val
             20                  25                  30

Thr Cys Val Val Val Asp Val Ser Gln Glu Asp Pro Glu Val Gln Phe
```

```
                    35                  40                  45
Asn Trp Tyr Val Asp Gly Val Glu Val His Asn Ala Lys Thr Lys Pro
 50                  55                  60

Arg Glu Glu Gln Phe Asn Ser Thr Tyr Arg Val Val Ser Val Leu Thr
 65                  70                  75                  80

Val Leu His Gln Asp Trp Leu Asn Gly Lys Glu Tyr Lys Cys Lys Val
                 85                  90                  95

Ser Asn Lys Gly Leu Pro Ser Ser Ile Glu Lys Thr Ile Ser Lys Ala
                100                 105                 110

Lys Gly Gln Pro Arg Glu Pro Gln Val Tyr Thr Leu Pro Pro Ser Gln
                115                 120                 125

Glu Glu Met Thr Lys Asn Gln Val Ser Leu Thr Cys Leu Val Lys Gly
                130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Arg Leu Thr Val Asp Lys Ser Arg Trp Gln Glu
                180                 185                 190

Gly Asn Val Phe Ser Cys Ser Val Met His Glu Ala Leu His Asn His
                195                 200                 205

Tyr Thr Gln Lys Ser Leu Ser Leu Ser Leu Gly Lys
                210                 215                 220

<210> SEQ ID NO 14
<211> LENGTH: 15
<212> TYPE: PRT
<213> ORGANISM: Homo sapiens

<400> SEQUENCE: 14

Glu Pro Lys Ser Cys Asp Lys Thr His Thr Cys Pro Pro Cys Pro
1               5                  10                  15

<210> SEQ ID NO 15
<211> LENGTH: 12
<212> TYPE: PRT
<213> ORGANISM: Homo sapiens

<400> SEQUENCE: 15

Glu Arg Lys Cys Cys Val Glu Cys Pro Pro Cys Pro
1               5                  10

<210> SEQ ID NO 16
<211> LENGTH: 62
<212> TYPE: PRT
<213> ORGANISM: Homo sapiens

<400> SEQUENCE: 16

Glu Leu Lys Thr Pro Leu Gly Asp Thr Thr His Thr Cys Pro Arg Cys
1               5                  10                  15

Pro Glu Pro Lys Ser Cys Asp Thr Pro Pro Pro Cys Pro Arg Cys Pro
                20                  25                  30

Glu Pro Lys Ser Cys Asp Thr Pro Pro Pro Cys Pro Arg Cys Pro Glu
                35                  40                  45

Pro Lys Ser Cys Asp Thr Pro Pro Pro Cys Pro Arg Cys Pro
                50                  55                  60

<210> SEQ ID NO 17
<211> LENGTH: 12
```

```
<212> TYPE: PRT
<213> ORGANISM: Homo sapiens

<400> SEQUENCE: 17

Glu Ser Lys Tyr Gly Pro Pro Cys Pro Ser Cys Pro
1               5                   10

<210> SEQ ID NO 18
<211> LENGTH: 3
<212> TYPE: PRT
<213> ORGANISM: Homo sapiens

<400> SEQUENCE: 18

Ser Cys Pro
1

<210> SEQ ID NO 19
<211> LENGTH: 4
<212> TYPE: PRT
<213> ORGANISM: Homo sapiens

<400> SEQUENCE: 19

Pro Ser Cys Pro
1

<210> SEQ ID NO 20
<211> LENGTH: 5
<212> TYPE: PRT
<213> ORGANISM: Homo sapiens

<400> SEQUENCE: 20

Cys Pro Ser Cys Pro
1               5

<210> SEQ ID NO 21
<211> LENGTH: 2
<212> TYPE: PRT
<213> ORGANISM: Homo sapiens

<400> SEQUENCE: 21

Cys Pro
1

<210> SEQ ID NO 22
<211> LENGTH: 699
<212> TYPE: DNA
<213> ORGANISM: Homo sapiens
<220> FEATURE:
<221> NAME/KEY: CDS
<222> LOCATION: (1)..(699)

<400> SEQUENCE: 22 atg gag ccc aaa tct tgt gac aaa act cac aca tgc cca ccg tgc cca      48
Met Glu Pro Lys Ser Cys Asp Lys Thr His Thr Cys Pro Pro Cys Pro
1               5                   10                  15 gca cct gaa ctc ctg ggg gga ccg tca gtc ttc ctc ttc ccc cca aaa      96
Ala Pro Glu Leu Leu Gly Gly Pro Ser Val Phe Leu Phe Pro Pro Lys
                20                  25                  30 ccc aag gac acc ctc atg atc tcc cgg acc cct gag gtc aca tgc gtg     144
Pro Lys Asp Thr Leu Met Ile Ser Arg Thr Pro Glu Val Thr Cys Val
            35                  40                  45 gtg gtg gac gtg agc cac gaa gac cct gag gtc aag ttc aac tgg tac     192
Val Val Asp Val Ser His Glu Asp Pro Glu Val Lys Phe Asn Trp Tyr
        50                  55                  60 gtg gac ggc gtg gag gtg cat aat gcc aag aca aag ccg cgg gag gag     240
```

```
Val Asp Gly Val Glu Val His Asn Ala Lys Thr Lys Pro Arg Glu Glu
 65                  70                  75                  80 cag tac aac agc acg tac cgt gtg gtc agc gtc ctc acc gtc ctg cac      288
Gln Tyr Asn Ser Thr Tyr Arg Val Val Ser Val Leu Thr Val Leu His
                 85                  90                  95 cag gac tgg ctg aat ggc aag gag tac aag tgc aag gtc tcc aac aaa      336
Gln Asp Trp Leu Asn Gly Lys Glu Tyr Lys Cys Lys Val Ser Asn Lys
             100                 105                 110 gcc ctc cca gcc ccc atc gag aaa acc atc tcc aaa gcc aaa ggg cag      384
Ala Leu Pro Ala Pro Ile Glu Lys Thr Ile Ser Lys Ala Lys Gly Gln
         115                 120                 125 ccc cga gag cca cag gtg tac acc ctg ccc cca tcc cgg gat gag ctg      432
Pro Arg Glu Pro Gln Val Tyr Thr Leu Pro Pro Ser Arg Asp Glu Leu
130                 135                 140 acc aag aac cag gtc agc ctg acc tgc ctg gtc aaa ggc ttc tat ccc      480
Thr Lys Asn Gln Val Ser Leu Thr Cys Leu Val Lys Gly Phe Tyr Pro
145                 150                 155                 160 agc gac atc gcc gtg gag tgg gag agc aat ggg cag ccg gag aac aac      528
Ser Asp Ile Ala Val Glu Trp Glu Ser Asn Gly Gln Pro Glu Asn Asn
                165                 170                 175 tac aag acc acg cct ccc gtg ctg gac tcc gac ggc tcc ttc ttc ctc      576
Tyr Lys Thr Thr Pro Pro Val Leu Asp Ser Asp Gly Ser Phe Phe Leu
            180                 185                 190 tac agc aag ctc acc gtg gac aag agc agg tgg cag cag ggg aac gtc      624
Tyr Ser Lys Leu Thr Val Asp Lys Ser Arg Trp Gln Gln Gly Asn Val
        195                 200                 205 ttc tca tgc tcc gtg atg cat gag gct ctg cac aac cac tac acg cag      672
Phe Ser Cys Ser Val Met His Glu Ala Leu His Asn His Tyr Thr Gln
210                 215                 220 aag agc ctc tcc ctg tct ccg ggt aaa                                  699
Lys Ser Leu Ser Leu Ser Pro Gly Lys
225                 230

<210> SEQ ID NO 23
<211> LENGTH: 233
<212> TYPE: PRT
<213> ORGANISM: Homo sapiens

<400> SEQUENCE: 23

Met Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160
```

```
Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
        180                 185                 190

Tyr Ser Lys Leu Thr Val Asp Lys Ser Arg Trp Gln Gln Gly Asn Val
    195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 24
<211> LENGTH: 690
<212> TYPE: DNA
<213> ORGANISM: Homo sapiens
<220> FEATURE:
<221> NAME/KEY: CDS
<222> LOCATION: (1)..(690)

<400> SEQUENCE: 24
```

| | | | | | | | | | | | | | | | | |
|---|---|---|---|---|---|---|---|---|---|---|---|---|---|---|---|---|
| atg | tct | tgt | gac | aaa | act | cac | aca | tgc | cca | ccg | tgc | cca | gca | cct | gaa | 48 |
| Met | Ser | Cys | Asp | Lys | Thr | His | Thr | Cys | Pro | Pro | Cys | Pro | Ala | Pro | Glu | |
| 1 | | | | 5 | | | | | 10 | | | | | 15 | | |
| ctc | ctg | ggg | gga | ccg | tca | gtc | ttc | ctc | ttc | ccc | cca | aaa | ccc | aag | gac | 96 |
| Leu | Leu | Gly | Gly | Pro | Ser | Val | Phe | Leu | Phe | Pro | Pro | Lys | Pro | Lys | Asp | |
| | | | 20 | | | | | 25 | | | | | 30 | | | |
| acc | ctc | atg | atc | tcc | cgg | acc | cct | gag | gtc | aca | tgc | gtg | gtg | gtg | gac | 144 |
| Thr | Leu | Met | Ile | Ser | Arg | Thr | Pro | Glu | Val | Thr | Cys | Val | Val | Val | Asp | |
| | | | 35 | | | | 40 | | | | | 45 | | | | |
| gtg | agc | cac | gaa | gac | cct | gag | gtc | aag | ttc | aac | tgg | tac | gtg | gac | ggc | 192 |
| Val | Ser | His | Glu | Asp | Pro | Glu | Val | Lys | Phe | Asn | Trp | Tyr | Val | Asp | Gly | |
| | 50 | | | | | 55 | | | | | 60 | | | | | |
| gtg | gag | gtg | cat | aat | gcc | aag | aca | aag | ccg | cgg | gag | gag | cag | tac | aac | 240 |
| Val | Glu | Val | His | Asn | Ala | Lys | Thr | Lys | Pro | Arg | Glu | Glu | Gln | Tyr | Asn | |
| 65 | | | | 70 | | | | | 75 | | | | | 80 | | |
| agc | acg | tac | cgt | gtg | gtc | agc | gtc | ctc | acc | gtc | ctg | cac | cag | gac | tgg | 288 |
| Ser | Thr | Tyr | Arg | Val | Val | Ser | Val | Leu | Thr | Val | Leu | His | Gln | Asp | Trp | |
| | | | | 85 | | | | | 90 | | | | | 95 | | |
| ctg | aat | ggc | aag | gag | tac | aag | tgc | aag | gtc | tcc | aac | aaa | gcc | ctc | cca | 336 |
| Leu | Asn | Gly | Lys | Glu | Tyr | Lys | Cys | Lys | Val | Ser | Asn | Lys | Ala | Leu | Pro | |
| | | | 100 | | | | | 105 | | | | | 110 | | | |
| gcc | ccc | atc | gag | aaa | acc | atc | tcc | aaa | gcc | aaa | ggg | cag | ccc | cga | gag | 384 |
| Ala | Pro | Ile | Glu | Lys | Thr | Ile | Ser | Lys | Ala | Lys | Gly | Gln | Pro | Arg | Glu | |
| | | | 115 | | | | 120 | | | | | 125 | | | | |
| cca | cag | gtg | tac | acc | ctg | ccc | cca | tcc | cgg | gat | gag | ctg | acc | aag | aac | 432 |
| Pro | Gln | Val | Tyr | Thr | Leu | Pro | Pro | Ser | Arg | Asp | Glu | Leu | Thr | Lys | Asn | |
| | | 130 | | | | | 135 | | | | | 140 | | | | |
| cag | gtc | agc | ctg | acc | tgc | ctg | gtc | aaa | ggc | ttc | tat | ccc | agc | gac | atc | 480 |
| Gln | Val | Ser | Leu | Thr | Cys | Leu | Val | Lys | Gly | Phe | Tyr | Pro | Ser | Asp | Ile | |
| 145 | | | | 150 | | | | | 155 | | | | | 160 | | |
| gcc | gtg | gag | tgg | gag | agc | aat | ggg | cag | ccg | gag | aac | aac | tac | aag | acc | 528 |
| Ala | Val | Glu | Trp | Glu | Ser | Asn | Gly | Gln | Pro | Glu | Asn | Asn | Tyr | Lys | Thr | |
| | | | | 165 | | | | | 170 | | | | | 175 | | |
| acg | cct | ccc | gtg | ctg | gac | tcc | gac | ggc | tcc | ttc | ttc | ctc | tac | agc | aag | 576 |
| Thr | Pro | Pro | Val | Leu | Asp | Ser | Asp | Gly | Ser | Phe | Phe | Leu | Tyr | Ser | Lys | |
| | | | 180 | | | | | 185 | | | | | 190 | | | |
| ctc | acc | gtg | gac | aag | agc | agg | tgg | cag | cag | ggg | aac | gtc | ttc | tca | tgc | 624 |
| Leu | Thr | Val | Asp | Lys | Ser | Arg | Trp | Gln | Gln | Gly | Asn | Val | Phe | Ser | Cys | |
| | | | | 195 | | | | | 200 | | | | | 205 | | |
| tcc | gtg | atg | cat | gag | gct | ctg | cac | aac | cac | tac | acg | cag | aag | agc | ctc | 672 |

```
Ser Val Met His Glu Ala Leu His Asn His Tyr Thr Gln Lys Ser Leu
        210                 215                 220 tcc ctg tct ccg ggt aaa                                              690
Ser Leu Ser Pro Gly Lys
225                 230

<210> SEQ ID NO 25
<211> LENGTH: 230
<212> TYPE: PRT
<213> ORGANISM: Homo sapiens

<400> SEQUENCE: 25

Met Ser Cys Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
                20                  25                  30

Thr Leu Met Ile Ser Arg Thr Pro Glu Val Thr Cys Val Val Val Asp
            35                  40                  45

Val Ser His Glu Asp Pro Glu Val Lys Phe Asn Trp Tyr Val Asp Gly
        50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
            100                 105                 110

Ala Pro Ile Glu Lys Thr Ile Ser Lys Ala Lys Gly Gln Pro Arg Glu
        115                 120                 125

Pro Gln Val Tyr Thr Leu Pro Pro Ser Arg Asp Glu Leu Thr Lys Asn
130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
            180                 185                 190

Leu Thr Val Asp Lys Ser Arg Trp Gln Gln Gly Asn Val Phe Ser Cys
        195                 200                 205

Ser Val Met His Glu Ala Leu His Asn His Tyr Thr Gln Lys Ser Leu
210                 215                 220

Ser Leu Ser Pro Gly Lys
225                 230

<210> SEQ ID NO 26
<211> LENGTH: 684
<212> TYPE: DNA
<213> ORGANISM: Homo sapiens
<220> FEATURE:
<221> NAME/KEY: CDS
<222> LOCATION: (1)..(684)

<400> SEQUENCE: 26 atg gac aaa act cac aca tgc cca ccg tgc cca gca cct gaa ctc ctg    48
Met Asp Lys Thr His Thr Cys Pro Pro Cys Pro Ala Pro Glu Leu Leu
1               5                   10                  15 ggg gga ccg tca gtc ttc ctc ttc ccc cca aaa ccc aag gac acc ctc    96
Gly Gly Pro Ser Val Phe Leu Phe Pro Pro Lys Pro Lys Asp Thr Leu
                20                  25                  30 atg atc tcc cgg acc cct gag gtc aca tgc gtg gtg gtg gac gtg agc   144
```

```
Met Ile Ser Arg Thr Pro Glu Val Thr Cys Val Val Asp Val Ser
        35                  40                  45 cac gaa gac cct gag gtc aag ttc aac tgg tac gtg gac ggc gtg gag      192
His Glu Asp Pro Glu Val Lys Phe Asn Trp Tyr Val Asp Gly Val Glu
        50                  55                  60 gtg cat aat gcc aag aca aag ccg cgg gag gag cag tac aac agc acg      240
Val His Asn Ala Lys Thr Lys Pro Arg Glu Glu Gln Tyr Asn Ser Thr
65                  70                  75                  80 tac cgt gtg gtc agc gtc ctc acc gtc ctg cac cag gac tgg ctg aat      288
Tyr Arg Val Val Ser Val Leu Thr Val Leu His Gln Asp Trp Leu Asn
                85                  90                  95 ggc aag gag tac aag tgc aag gtc tcc aac aaa gcc ctc cca gcc ccc      336
Gly Lys Glu Tyr Lys Cys Lys Val Ser Asn Lys Ala Leu Pro Ala Pro
            100                 105                 110 atc gag aaa acc atc tcc aaa gcc aaa ggg cag ccc cga gag cca cag      384
Ile Glu Lys Thr Ile Ser Lys Ala Lys Gly Gln Pro Arg Glu Pro Gln
        115                 120                 125 gtg tac acc ctg ccc cca tcc cgg gat gag ctg acc aag aac cag gtc      432
Val Tyr Thr Leu Pro Pro Ser Arg Asp Glu Leu Thr Lys Asn Gln Val
    130                 135                 140 agc ctg acc tgc ctg gtc aaa ggc ttc tat ccc agc gac atc gcc gtg      480
Ser Leu Thr Cys Leu Val Lys Gly Phe Tyr Pro Ser Asp Ile Ala Val
145                 150                 155                 160 gag tgg gag agc aat ggg cag ccg gag aac aac tac aag acc acg cct      528
Glu Trp Glu Ser Asn Gly Gln Pro Glu Asn Asn Tyr Lys Thr Thr Pro
                165                 170                 175 ccc gtg ctg gac tcc gac ggc tcc ttc ttc ctc tac agc aag ctc acc      576
Pro Val Leu Asp Ser Asp Gly Ser Phe Phe Leu Tyr Ser Lys Leu Thr
            180                 185                 190 gtg gac aag agc agg tgg cag cag ggg aac gtc ttc tca tgc tcc gtg      624
Val Asp Lys Ser Arg Trp Gln Gln Gly Asn Val Phe Ser Cys Ser Val
        195                 200                 205 atg cat gag gct ctg cac aac cac tac acg cag aag agc ctc tcc ctg      672
Met His Glu Ala Leu His Asn His Tyr Thr Gln Lys Ser Leu Ser Leu
    210                 215                 220 tct ccg ggt aaa                                                       684
Ser Pro Gly Lys
225

<210> SEQ ID NO 27
<211> LENGTH: 228
<212> TYPE: PRT
<213> ORGANISM: Homo sapiens

<400> SEQUENCE: 27

Met Asp Lys Thr His Thr Cys Pro Pro Cys Pro Ala Pro Glu Leu Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Lys Phe Asn Trp Tyr Val Asp Gly Val Glu
    50                  55                  60

Val His Asn Ala Lys Thr Lys Pro Arg Glu Glu Gln Tyr Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110
```

```
Ile Glu Lys Thr Ile Ser Lys Ala Lys Gly Gln Pro Arg Glu Pro Gln
        115                 120                 125

Val Tyr Thr Leu Pro Pro Ser Arg Asp Glu Leu Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
                180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
210                 215                 220

Ser Pro Gly Lys
225

<210> SEQ ID NO 28
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 28 atg tgc cca gca cct gaa ctc ctg ggg gga ccg tca gtc ttc ctc ttc          48
Met Cys Pro Ala Pro Glu Leu Leu Gly Gly Pro Ser Val Phe Leu Phe
1               5                   10                  15 ccc cca aaa ccc aag gac acc ctc atg atc tcc cgg acc cct gag gtc          96
Pro Pro Lys Pro Lys Asp Thr Leu Met Ile Ser Arg Thr Pro Glu Val
            20                  25                  30 aca tgc gtg gtg gtg gac gtg agc cac gaa gac cct gag gtc aag ttc         144
Thr Cys Val Val Val Asp Val Ser His Glu Asp Pro Glu Val Lys Phe
        35                  40                  45 aac tgg tac gtg gac ggc gtg gag gtg cat aat gcc aag aca aag ccg         192
Asn Trp Tyr Val Asp Gly Val Glu Val His Asn Ala Lys Thr Lys Pro
    50                  55                  60 cgg gag gag cag tac aac agc acg tac cgt gtg gtc agc gtc ctc acc         240
Arg Glu Glu Gln Tyr Asn Ser Thr Tyr Arg Val Val Ser Val Leu Thr
65                  70                  75                  80 gtc ctg cac cag gac tgg ctg aat ggc aag gag tac aag tgc aag gtc         288
Val Leu His Gln Asp Trp Leu Asn Gly Lys Glu Tyr Lys Cys Lys Val
                85                  90                  95 tcc aac aaa gcc ctc cca gcc ccc atc gag aaa acc atc tcc aaa gcc         336
Ser Asn Lys Ala Leu Pro Ala Pro Ile Glu Lys Thr Ile Ser Lys Ala
            100                 105                 110 aaa ggg cag ccc cga gag cca cag gtg tac acc ctg ccc cca tcc cgg         384
Lys Gly Gln Pro Arg Glu Pro Gln Val Tyr Thr Leu Pro Pro Ser Arg
        115                 120                 125 gat gag ctg acc aag aac cag gtc agc ctg acc tgc ctg gtc aaa ggc         432
Asp Glu Leu Thr Lys Asn Gln Val Ser Leu Thr Cys Leu Val Lys Gly
130                 135                 140 ttc tat ccc agc gac atc gcc gtg gag tgg gag agc aat ggg cag ccg         480
Phe Tyr Pro Ser Asp Ile Ala Val Glu Trp Glu Ser Asn Gly Gln Pro
145                 150                 155                 160 gag aac aac tac aag acc acg cct ccc gtg ctg gac tcc gac ggc tcc         528
Glu Asn Asn Tyr Lys Thr Thr Pro Pro Val Leu Asp Ser Asp Gly Ser
                165                 170                 175 ttc ttc ctc tac agc aag ctc acc gtg gac aag agc agg tgg cag cag         576
```

```
                Phe Phe Leu Tyr Ser Lys Leu Thr Val Asp Lys Ser Arg Trp Gln Gln
                            180                 185                 190 ggg aac gtc ttc tca tgc tcc gtg atg cat gag gct ctg cac aac cac                  624
Gly Asn Val Phe Ser Cys Ser Val Met His Glu Ala Leu His Asn His
            195                 200                 205 tac acg cag aag agc ctc tcc ctg tct ccg ggt aaa                                  660
Tyr Thr Gln Lys Ser Leu Ser Leu Ser Pro Gly Lys
    210                 215                 220

<210> SEQ ID NO 29
<211> LENGTH: 220
<212> TYPE: PRT
<213> ORGANISM: Homo sapiens

<400> SEQUENCE: 29

Met Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
                20                  25                  30

Thr Cys Val Val Val Asp Val Ser His Glu Asp Pro Glu Val Lys Phe
            35                  40                  45

Asn Trp Tyr Val Asp Gly Val Glu Val His Asn Ala Lys Thr Lys Pro
        50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
                100                 105                 110

Lys Gly Gln Pro Arg Glu Pro Gln Val Tyr Thr Leu Pro Pro Ser Arg
            115                 120                 125

Asp Glu Leu Thr Lys Asn Gln Val Ser Leu Thr Cys Leu Val Lys Gly
        130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 30
<211> LENGTH: 696
<212> TYPE: DNA
<213> ORGANISM: Homo sapiens
<220> FEATURE:
<221> NAME/KEY: CDS
<222> LOCATION: (1)..(696)

<400> SEQUENCE: 30 atg ccc aaa tct tgt gac aaa act cac aca tgc cca ccg tgc cca gca                 48
Met Pro Lys Ser Cys Asp Lys Thr His Thr Cys Pro Pro Cys Pro Ala
1               5                   10                  15 cct gaa ctc ctg ggg gga ccg tca gtc ttc ctc ttc ccc cca aaa ccc                 96
Pro Glu Leu Leu Gly Gly Pro Ser Val Phe Leu Phe Pro Pro Lys Pro
            20                  25                  30
```

```
aag gac acc ctc atg atc tcc cgg acc cct gag gtc aca tgc gtg gtg     144
Lys Asp Thr Leu Met Ile Ser Arg Thr Pro Glu Val Thr Cys Val Val
         35                  40                  45 gtg gac gtg agc cac gaa gac cct gag gtc aag ttc aac tgg tac gtg     192
Val Asp Val Ser His Glu Asp Pro Glu Val Lys Phe Asn Trp Tyr Val
     50                  55                  60 gac ggc gtg gag gtg cat aat gcc aag aca aag ccg cgg gag gag cag     240
Asp Gly Val Glu Val His Asn Ala Lys Thr Lys Pro Arg Glu Glu Gln
65                  70                  75                  80 tac aac agc acg tac cgt gtg gtc agc gtc ctc acc gtc ctg cac cag     288
Tyr Asn Ser Thr Tyr Arg Val Val Ser Val Leu Thr Val Leu His Gln
                 85                  90                  95 gac tgg ctg aat ggc aag gag tac aag tgc aag gtc tcc aac aaa gcc     336
Asp Trp Leu Asn Gly Lys Glu Tyr Lys Cys Lys Val Ser Asn Lys Ala
            100                 105                 110 ctc cca gcc ccc atc gag aaa acc atc tcc aaa gcc aaa ggg cag ccc     384
Leu Pro Ala Pro Ile Glu Lys Thr Ile Ser Lys Ala Lys Gly Gln Pro
        115                 120                 125 cga gag cca cag gtg tac acc ctg ccc cca tcc cgg gat gag ctg acc     432
Arg Glu Pro Gln Val Tyr Thr Leu Pro Pro Ser Arg Asp Glu Leu Thr
    130                 135                 140 aag aac cag gtc agc ctg acc tgc ctg gtc aaa ggc ttc tat ccc agc     480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac     528
Asp Ile Ala Val Glu Trp Glu Ser Asn Gly Gln Pro Glu Asn Asn Tyr
                165                 170                 175 aag acc acg cct ccc gtg ctg gac tcc gac ggc tcc ttc ttc ctc tac     576
Lys Thr Thr Pro Pro Val Leu Asp Ser Asp Gly Ser Phe Phe Leu Tyr
            180                 185                 190 agc aag ctc acc gtg gac aag agc agg tgg cag cag ggg aac gtc ttc     624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag     672
Ser Cys Ser Val Met His Glu Ala Leu His Asn His Tyr Thr Gln Lys
    210                 215                 220 agc ctc tcc ctg tct ccg ggt aaa                                     696
Ser Leu Ser Leu Ser Pro Gly Lys
225                 230

<210> SEQ ID NO 31
<211> LENGTH: 232
<212> TYPE: PRT
<213> ORGANISM: Homo sapiens

<400> SEQUENCE: 31

Met Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

```
Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
    195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 32
<211> LENGTH: 669
<212> TYPE: DNA
<213> ORGANISM: Homo sapiens
<220> FEATURE:
<221> NAME/KEY: CDS
<222> LOCATION: (1)..(669)

<400> SEQUENCE: 32 atg tgc cca ccg tgc cca gca cct gaa ctc ctg ggg gga ccg tca gtc      48
Met Cys Pro Pro Cys Pro Ala Pro Glu Leu Leu Gly Gly Pro Ser Val
1               5                   10                  15 ttc ctc ttc ccc cca aaa ccc aag gac acc ctc atg atc tcc cgg acc      96
Phe Leu Phe Pro Pro Lys Pro Lys Asp Thr Leu Met Ile Ser Arg Thr
            20                  25                  30 cct gag gtc aca tgc gtg gtg gtg gac gtg agc cac gaa gac cct gag     144
Pro Glu Val Thr Cys Val Val Val Asp Val Ser His Glu Asp Pro Glu
        35                  40                  45 gtc aag ttc aac tgg tac gtg gac ggc gtg gag gtg cat aat gcc aag     192
Val Lys Phe Asn Trp Tyr Val Asp Gly Val Glu Val His Asn Ala Lys
    50                  55                  60 aca aag ccg cgg gag gag cag tac aac agc acg tac cgt gtg gtc agc     240
Thr Lys Pro Arg Glu Glu Gln Tyr Asn Ser Thr Tyr Arg Val Val Ser
65                  70                  75                  80 gtc ctc acc gtc ctg cac cag gac tgg ctg aat ggc aag gag tac aag     288
Val Leu Thr Val Leu His Gln Asp Trp Leu Asn Gly Lys Glu Tyr Lys
                85                  90                  95 tgc aag gtc tcc aac aaa gcc ctc cca gcc ccc atc gag aaa acc atc     336
Cys Lys Val Ser Asn Lys Ala Leu Pro Ala Pro Ile Glu Lys Thr Ile
            100                 105                 110 tcc aaa gcc aaa ggg cag ccc cga gag cca cag gtg tac acc ctg ccc     384
Ser Lys Ala Lys Gly Gln Pro Arg Glu Pro Gln Val Tyr Thr Leu Pro
        115                 120                 125 cca tcc cgg gat gag ctg acc aag aac cag gtc agc ctg acc tgc ctg     432
Pro Ser Arg Asp Glu Leu Thr Lys Asn Gln Val Ser Leu Thr Cys Leu
    130                 135                 140 gtc aaa ggc ttc tat ccc agc gac atc gcc gtg gag tgg gag agc aat     480
Val Lys Gly Phe Tyr Pro Ser Asp Ile Ala Val Glu Trp Glu Ser Asn
145                 150                 155                 160 ggg cag ccg gag aac aac tac aag acc acg cct ccc gtg ctg gac tcc     528
Gly Gln Pro Glu Asn Asn Tyr Lys Thr Thr Pro Pro Val Leu Asp Ser
                165                 170                 175
```

```
gac ggc tcc ttc ttc ctc tac agc aag ctc acc gtg gac aag agc agg      576
Asp Gly Ser Phe Phe Leu Tyr Ser Lys Leu Thr Val Asp Lys Ser Arg
            180                 185                 190 tgg cag cag ggg aac gtc ttc tca tgc tcc gtg atg cat gag gct ctg      624
Trp Gln Gln Gly Asn Val Phe Ser Cys Ser Val Met His Glu Ala Leu
        195                 200                 205 cac aac cac tac acg cag aag agc ctc tcc ctg tct ccg ggt aaa          669
His Asn His Tyr Thr Gln Lys Ser Leu Ser Leu Ser Pro Gly Lys
    210                 215                 220
```

<210> SEQ ID NO 33
<211> LENGTH: 223
<212> TYPE: PRT
<213> ORGANISM: Homo sapiens

<400> SEQUENCE: 33

```
Met Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 34
<211> LENGTH: 666
<212> TYPE: DNA
<213> ORGANISM: Homo sapiens
<220> FEATURE:
<221> NAME/KEY: CDS
<222> LOCATION: (1)..(666)

<400> SEQUENCE: 34

```
atg cca ccg tgc cca gca cct gaa ctc ctg ggg gga ccg tca gtc ttc      48
Met Pro Pro Cys Pro Ala Pro Glu Leu Leu Gly Gly Pro Ser Val Phe
1               5                   10                  15 ctc ttc ccc cca aaa ccc aag gac acc ctc atg atc tcc cgg acc cct      96
Leu Phe Pro Pro Lys Pro Lys Asp Thr Leu Met Ile Ser Arg Thr Pro
            20                  25                  30
```

```
gag gtc aca tgc gtg gtg gtg gac gtg agc cac gaa gac cct gag gtc      144
Glu Val Thr Cys Val Val Val Asp Val Ser His Glu Asp Pro Glu Val
         35                  40                  45 aag ttc aac tgg tac gtg gac ggc gtg gag gtg cat aat gcc aag aca      192
Lys Phe Asn Trp Tyr Val Asp Gly Val Glu Val His Asn Ala Lys Thr
 50                  55                  60 aag ccg cgg gag gag cag tac aac agc acg tac cgt gtg gtc agc gtc      240
Lys Pro Arg Glu Glu Gln Tyr Asn Ser Thr Tyr Arg Val Val Ser Val
 65                  70                  75                  80 ctc acc gtc ctg cac cag gac tgg ctg aat ggc aag gag tac aag tgc      288
Leu Thr Val Leu His Gln Asp Trp Leu Asn Gly Lys Glu Tyr Lys Cys
                 85                  90                  95 aag gtc tcc aac aaa gcc ctc cca gcc ccc atc gag aaa acc atc tcc      336
Lys Val Ser Asn Lys Ala Leu Pro Ala Pro Ile Glu Lys Thr Ile Ser
            100                 105                 110 aaa gcc aaa ggg cag ccc cga gag cca cag gtg tac acc ctg ccc cca      384
Lys Ala Lys Gly Gln Pro Arg Glu Pro Gln Val Tyr Thr Leu Pro Pro
        115                 120                 125 tcc cgg gat gag ctg acc aag aac cag gtc agc ctg acc tgc ctg gtc      432
Ser Arg Asp Glu Leu Thr Lys Asn Gln Val Ser Leu Thr Cys Leu Val
    130                 135                 140 aaa ggc ttc tat ccc agc gac atc gcc gtg gag tgg gag agc aat ggg      480
Lys Gly Phe Tyr Pro Ser Asp Ile Ala Val Glu Trp Glu Ser Asn Gly
145                 150                 155                 160 cag ccg gag aac aac tac aag acc acg cct ccc gtg ctg gac tcc gac      528
Gln Pro Glu Asn Asn Tyr Lys Thr Thr Pro Pro Val Leu Asp Ser Asp
                165                 170                 175 ggc tcc ttc ttc ctc tac agc aag ctc acc gtg gac aag agc agg tgg      576
Gly Ser Phe Phe Leu Tyr Ser Lys Leu Thr Val Asp Lys Ser Arg Trp
            180                 185                 190 cag cag ggg aac gtc ttc tca tgc tcc gtg atg cat gag gct ctg cac      624
Gln Gln Gly Asn Val Phe Ser Cys Ser Val Met His Glu Ala Leu His
        195                 200                 205 aac cac tac acg cag aag agc ctc tcc ctg tct ccg ggt aaa             666
Asn His Tyr Thr Gln Lys Ser Leu Ser Leu Ser Pro Gly Lys
    210                 215                 220

<210> SEQ ID NO 35
<211> LENGTH: 222
<212> TYPE: PRT
<213> ORGANISM: Homo sapiens

<400> SEQUENCE: 35

Met Pro Pro Cys Pro Ala Pro Glu Leu Leu Gly Gly Pro Ser Val Phe
 1               5                  10                  15

Leu Phe Pro Pro Lys Pro Lys Asp Thr Leu Met Ile Ser Arg Thr Pro
             20                  25                  30

Glu Val Thr Cys Val Val Val Asp Val Ser His Glu Asp Pro Glu Val
         35                  40                  45

Lys Phe Asn Trp Tyr Val Asp Gly Val Glu Val His Asn Ala Lys Thr
 50                  55                  60

Lys Pro Arg Glu Glu Gln Tyr Asn Ser Thr Tyr Arg Val Val Ser Val
 65                  70                  75                  80

Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125
```

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 36
<211> LENGTH: 663
<212> TYPE: DNA
<213> ORGANISM: Homo sapiens
<220> FEATURE:
<221> NAME/KEY: CDS
<222> LOCATION: (1)..(663)

<400> SEQUENCE: 36 atg ccg tgc cca gca cct gaa ctc ctg ggg gga ccg tca gtc ttc ctc       48
Met Pro Cys Pro Ala Pro Glu Leu Leu Gly Gly Pro Ser Val Phe Leu
1               5                   10                  15 ttc ccc cca aaa ccc aag gac acc ctc atg atc tcc cgg acc cct gag       96
Phe Pro Pro Lys Pro Lys Asp Thr Leu Met Ile Ser Arg Thr Pro Glu
                20                  25                  30 gtc aca tgc gtg gtg gtg gac gtg agc cac gaa gac cct gag gtc aag      144
Val Thr Cys Val Val Val Asp Val Ser His Glu Asp Pro Glu Val Lys
            35                  40                  45 ttc aac tgg tac gtg gac ggc gtg gag gtg cat aat gcc aag aca aag      192
Phe Asn Trp Tyr Val Asp Gly Val Glu Val His Asn Ala Lys Thr Lys
        50                  55                  60 ccg cgg gag gag cag tac aac agc acg tac cgt gtg gtc agc gtc ctc      240
Pro Arg Glu Glu Gln Tyr Asn Ser Thr Tyr Arg Val Val Ser Val Leu
65                  70                  75                  80 acc gtc ctg cac cag gac tgg ctg aat ggc aag gag tac aag tgc aag      288
Thr Val Leu His Gln Asp Trp Leu Asn Gly Lys Glu Tyr Lys Cys Lys
                85                  90                  95 gtc tcc aac aaa gcc ctc cca gcc ccc atc gag aaa acc atc tcc aaa      336
Val Ser Asn Lys Ala Leu Pro Ala Pro Ile Glu Lys Thr Ile Ser Lys
            100                 105                 110 gcc aaa ggg cag ccc cga gag cca cag gtg tac acc ctg ccc cca tcc      384
Ala Lys Gly Gln Pro Arg Glu Pro Gln Val Tyr Thr Leu Pro Pro Ser
        115                 120                 125 cgg gat gag ctg acc aag aac cag gtc agc ctg acc tgc ctg gtc aaa      432
Arg Asp Glu Leu Thr Lys Asn Gln Val Ser Leu Thr Cys Leu Val Lys
130                 135                 140 ggc ttc tat ccc agc gac atc gcc gtg gag tgg gag agc aat ggg cag      480
Gly Phe Tyr Pro Ser Asp Ile Ala Val Glu Trp Glu Ser Asn Gly Gln
145                 150                 155                 160 ccg gag aac aac tac aag acc acg cct ccc gtg ctg gac tcc gac ggc      528
Pro Glu Asn Asn Tyr Lys Thr Thr Pro Pro Val Leu Asp Ser Asp Gly
                165                 170                 175 tcc ttc ttc ctc tac agc aag ctc acc gtg gac aag agc agg tgg cag      576
Ser Phe Phe Leu Tyr Ser Lys Leu Thr Val Asp Lys Ser Arg Trp Gln
            180                 185                 190 cag ggg aac gtc ttc tca tgc tcc gtg atg cat gag gct ctg cac aac      624
Gln Gly Asn Val Phe Ser Cys Ser Val Met His Glu Ala Leu His Asn

```
cac tac acg cag aag agc ctc tcc ctg tct ccg ggt aaa          663
His Tyr Thr Gln Lys Ser Leu Ser Leu Ser Pro Gly Lys
    210                 215                 220
```

<210> SEQ ID NO 37
<211> LENGTH: 221
<212> TYPE: PRT
<213> ORGANISM: Homo sapiens

<400> SEQUENCE: 37

```
Met Pro Cys Pro Ala Pro Glu Leu Leu Gly Gly Pro Ser Val Phe Leu
1               5                   10                  15

Phe Pro Pro Lys Pro Lys Asp Thr Leu Met Ile Ser Arg Thr Pro Glu
            20                  25                  30

Val Thr Cys Val Val Val Asp Val Ser His Glu Asp Pro Glu Val Lys
        35                  40                  45

Phe Asn Trp Tyr Val Asp Gly Val Glu Val His Asn Ala Lys Thr Lys
    50                  55                  60

Pro Arg Glu Glu Gln Tyr Asn Ser Thr Tyr Arg Val Val Ser Val Leu
65                  70                  75                  80

Thr Val Leu His Gln Asp Trp Leu Asn Gly Lys Glu Tyr Lys Cys Lys
                85                  90                  95

Val Ser Asn Lys Ala Leu Pro Ala Pro Ile Glu Lys Thr Ile Ser Lys
            100                 105                 110

Ala Lys Gly Gln Pro Arg Glu Pro Gln Val Tyr Thr Leu Pro Pro Ser
        115                 120                 125

Arg Asp Glu Leu Thr Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys
    210                 215                 220
```

<210> SEQ ID NO 38
<211> LENGTH: 663
<212> TYPE: DNA
<213> ORGANISM: Homo sapiens
<220> FEATURE:
<221> NAME/KEY: CDS
<222> LOCATION: (1)..(663)

<400> SEQUENCE: 38

```
atg cca ccg tgc cca gca cct ccg gtg gcg gga ccg tca gtc ttc ctc    48
Met Pro Pro Cys Pro Ala Pro Pro Val Ala Gly Pro Ser Val Phe Leu
1               5                   10                  15 ttc ccc cca aaa ccc aag gac acc ctc atg atc tcc cgg acc cct gag    96
Phe Pro Pro Lys Pro Lys Asp Thr Leu Met Ile Ser Arg Thr Pro Glu
            20                  25                  30 gtc aca tgc gtg gtg gtg gac gtg agc cac gaa gac cct gag gtc cag   144
Val Thr Cys Val Val Val Asp Val Ser His Glu Asp Pro Glu Val Gln
        35                  40                  45 ttc aac tgg tac gtg gac ggc gtg gag gtg cat aat gcc aag aca aag   192
Phe Asn Trp Tyr Val Asp Gly Val Glu Val His Asn Ala Lys Thr Lys
```

```
Phe Asn Trp Tyr Val Asp Gly Val Glu Val His Asn Ala Lys Thr Lys
             50                  55                  60 ccg cgg gag gag cag ttt aac agc acg ttt cgt gtg gtc agc gtc ctc      240
Pro Arg Glu Glu Gln Phe Asn Ser Thr Phe Arg Val Val Ser Val Leu
 65                  70                  75                  80 acc gtc gtg cac cag gac tgg ctg aat ggc aag gag tac aag tgc aag      288
Thr Val Val His Gln Asp Trp Leu Asn Gly Lys Glu Tyr Lys Cys Lys
                     85                  90                  95 gtc tcc aac aaa ggc ctc cca gcc ccc atc gag aaa acc atc tcc aaa      336
Val Ser Asn Lys Gly Leu Pro Ala Pro Ile Glu Lys Thr Ile Ser Lys
                100                 105                 110 acc aaa ggg cag ccc cga gag cca cag gtg tac acc ctg ccc cca tcc      384
Thr Lys Gly Gln Pro Arg Glu Pro Gln Val Tyr Thr Leu Pro Pro Ser
            115                 120                 125 cgg gaa gag atg acc aag aac cag gtc agc ctg acc tgc ctg gtc aaa      432
Arg Glu Glu Met Thr Lys Asn Gln Val Ser Leu Thr Cys Leu Val Lys
        130                 135                 140 ggc ttc tat ccc agc gac atc gcc gtg gag tgg gag agc aat ggg cag      480
Gly Phe Tyr Pro Ser Asp Ile Ala Val Glu Trp Glu Ser Asn Gly Gln
145                 150                 155                 160 ccg gag aac aac tac aag acc acg cct ccc atg ctg gac tcc gac ggc      528
Pro Glu Asn Asn Tyr Lys Thr Thr Pro Pro Met Leu Asp Ser Asp Gly
                165                 170                 175 tcc ttc ttc ctc tac agc aag ctc acc gtg gac aag agc agg tgg cag      576
Ser Phe Phe Leu Tyr Ser Lys Leu Thr Val Asp Lys Ser Arg Trp Gln
            180                 185                 190 cag ggg aac gtc ttc tca tgc tcc gtg atg cat gag gct ctg cac aac      624
Gln Gly Asn Val Phe Ser Cys Ser Val Met His Glu Ala Leu His Asn
        195                 200                 205 cac tac acg cag aag agc ctc tcc ctg tct ccg ggt aaa                  663
His Tyr Thr Gln Lys Ser Leu Ser Leu Ser Pro Gly Lys
210                 215                 220

<210> SEQ ID NO 39
<211> LENGTH: 221
<212> TYPE: PRT
<213> ORGANISM: Homo sapiens

<400> SEQUENCE: 39

Met Pro Pro Cys Pro Ala Pro Pro Val Ala Gly Pro Ser Val Phe Leu
 1               5                  10                  15

Phe Pro Pro Lys Pro Lys Asp Thr Leu Met Ile Ser Arg Thr Pro Glu
                20                  25                  30

Val Thr Cys Val Val Val Asp Val Ser His Glu Asp Pro Glu Val Gln
            35                  40                  45

Phe Asn Trp Tyr Val Asp Gly Val Glu Val His Asn Ala Lys Thr Lys
        50                  55                  60

Pro Arg Glu Glu Gln Phe Asn Ser Thr Phe Arg Val Val Ser Val Leu
 65                 70                  75                  80

Thr Val Val His Gln Asp Trp Leu Asn Gly Lys Glu Tyr Lys Cys Lys
                85                  90                  95

Val Ser Asn Lys Gly Leu Pro Ala Pro Ile Glu Lys Thr Ile Ser Lys
            100                 105                 110

Thr Lys Gly Gln Pro Arg Glu Pro Gln Val Tyr Thr Leu Pro Pro Ser
        115                 120                 125

Arg Glu Glu Met Thr Lys Asn Gln Val Ser Leu Thr Cys Leu Val Lys
130                 135                 140

Gly Phe Tyr Pro Ser Asp Ile Ala Val Glu Trp Glu Ser Asn Gly Gln
145                 150                 155                 160
```

```
Pro Glu Asn Asn Tyr Lys Thr Thr Pro Pro Met Leu Asp Ser Asp Gly
            165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
            195                 200                 205

His Tyr Thr Gln Lys Ser Leu Ser Leu Ser Pro Gly Lys
    210                 215                 220

<210> SEQ ID NO 40
<211> LENGTH: 660
<212> TYPE: DNA
<213> ORGANISM: Homo sapiens
<220> FEATURE:
<221> NAME/KEY: CDS
<222> LOCATION: (1)..(660)

<400> SEQUENCE: 40
```

| | | | | | | | | | | | | | | | | |
|---|---|---|---|---|---|---|---|---|---|---|---|---|---|---|---|---|
| atg | ccg | tgc | cca | gca | cct | ccg | gtg | gcg | gga | ccg | tca | gtc | ttc | ctc | ttc | 48 |
| Met | Pro | Cys | Pro | Ala | Pro | Pro | Val | Ala | Gly | Pro | Ser | Val | Phe | Leu | Phe | |
| 1 | | | | 5 | | | | | 10 | | | | | 15 | | |
| ccc | cca | aaa | ccc | aag | gac | acc | ctc | atg | atc | tcc | cgg | acc | cct | gag | gtc | 96 |
| Pro | Pro | Lys | Pro | Lys | Asp | Thr | Leu | Met | Ile | Ser | Arg | Thr | Pro | Glu | Val | |
| | | | 20 | | | | 25 | | | | | 30 | | | | |
| aca | tgc | gtg | gtg | gtg | gac | gtg | agc | cac | gaa | gac | cct | gag | gtc | cag | ttc | 144 |
| Thr | Cys | Val | Val | Val | Asp | Val | Ser | His | Glu | Asp | Pro | Glu | Val | Gln | Phe | |
| | | 35 | | | | | 40 | | | | | 45 | | | | |
| aac | tgg | tac | gtg | gac | ggc | gtg | gag | gtg | cat | aat | gcc | aag | aca | aag | ccg | 192 |
| Asn | Trp | Tyr | Val | Asp | Gly | Val | Glu | Val | His | Asn | Ala | Lys | Thr | Lys | Pro | |
| | 50 | | | | | 55 | | | | | 60 | | | | | |
| cgg | gag | gag | cag | ttt | aac | agc | acg | ttt | cgt | gtg | gtc | agc | gtc | ctc | acc | 240 |
| Arg | Glu | Glu | Gln | Phe | Asn | Ser | Thr | Phe | Arg | Val | Val | Ser | Val | Leu | Thr | |
| 65 | | | | | 70 | | | | | 75 | | | | | 80 | |
| gtc | gtg | cac | cag | gac | tgg | ctg | aat | ggc | aag | gag | tac | aag | tgc | aag | gtc | 288 |
| Val | Val | His | Gln | Asp | Trp | Leu | Asn | Gly | Lys | Glu | Tyr | Lys | Cys | Lys | Val | |
| | | | | 85 | | | | | 90 | | | | | 95 | | |
| tcc | aac | aaa | ggc | ctc | cca | gcc | ccc | atc | gag | aaa | acc | atc | tcc | aaa | acc | 336 |
| Ser | Asn | Lys | Gly | Leu | Pro | Ala | Pro | Ile | Glu | Lys | Thr | Ile | Ser | Lys | Thr | |
| | | | 100 | | | | 105 | | | | | 110 | | | | |
| aaa | ggg | cag | ccc | cga | gag | cca | cag | gtg | tac | acc | ctg | ccc | cca | tcc | cgg | 384 |
| Lys | Gly | Gln | Pro | Arg | Glu | Pro | Gln | Val | Tyr | Thr | Leu | Pro | Pro | Ser | Arg | |
| | | | 115 | | | | 120 | | | | | 125 | | | | |
| gaa | gag | atg | acc | aag | aac | cag | gtc | agc | ctg | acc | tgc | ctg | gtc | aaa | ggc | 432 |
| Glu | Glu | Met | Thr | Lys | Asn | Gln | Val | Ser | Leu | Thr | Cys | Leu | Val | Lys | Gly | |
| | 130 | | | | | 135 | | | | | 140 | | | | | |
| ttc | tat | ccc | agc | gac | atc | gcc | gtg | gag | tgg | gag | agc | aat | ggg | cag | ccg | 480 |
| Phe | Tyr | Pro | Ser | Asp | Ile | Ala | Val | Glu | Trp | Glu | Ser | Asn | Gly | Gln | Pro | |
| 145 | | | | | 150 | | | | | 155 | | | | | 160 | |
| gag | aac | aac | tac | aag | acc | acg | cct | ccc | atg | ctg | gac | tcc | gac | ggc | tcc | 528 |
| Glu | Asn | Asn | Tyr | Lys | Thr | Thr | Pro | Pro | Met | Leu | Asp | Ser | Asp | Gly | Ser | |
| | | | | 165 | | | | | 170 | | | | | 175 | | |
| ttc | ttc | ctc | tac | agc | aag | ctc | acc | gtg | gac | aag | agc | agg | tgg | cag | cag | 576 |
| Phe | Phe | Leu | Tyr | Ser | Lys | Leu | Thr | Val | Asp | Lys | Ser | Arg | Trp | Gln | Gln | |
| | | | 180 | | | | | 185 | | | | | 190 | | | |
| ggg | aac | gtc | ttc | tca | tgc | tcc | gtg | atg | cat | gag | gct | ctg | cac | aac | cac | 624 |
| Gly | Asn | Val | Phe | Ser | Cys | Ser | Val | Met | His | Glu | Ala | Leu | His | Asn | His | |
| | | | 195 | | | | | 200 | | | | | 205 | | | |
| tac | acg | cag | aag | agc | ctc | tcc | ctg | tct | ccg | ggt | aaa | | | | | 660 |
| Tyr | Thr | Gln | Lys | Ser | Leu | Ser | Leu | Ser | Pro | Gly | Lys | | | | | |
| | 210 | | | | | 215 | | | | | 220 | | | | | |

<210> SEQ ID NO 41
<211> LENGTH: 220
<212> TYPE: PRT
<213> ORGANISM: Homo sapiens

<400> SEQUENCE: 41

Met Pro Cys Pro Ala Pro Pro Val Ala Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Gln Phe
        35                  40                  45

Asn Trp Tyr Val Asp Gly Val Glu Val His Asn Ala Lys Thr Lys Pro
    50                  55                  60

Arg Glu Glu Gln Phe Asn Ser Thr Phe Arg Val Val Ser Val Leu Thr
65                  70                  75                  80

Val Val His Gln Asp Trp Leu Asn Gly Lys Glu Tyr Lys Cys Lys Val
                85                  90                  95

Ser Asn Lys Gly Leu Pro Ala Pro Ile Glu Lys Thr Ile Ser Lys Thr
            100                 105                 110

Lys Gly Gln Pro Arg Glu Pro Gln Val Tyr Thr Leu Pro Pro Ser Arg
        115                 120                 125

Glu Glu Met Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Met Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 42
<211> LENGTH: 657
<212> TYPE: DNA
<213> ORGANISM: Homo sapiens
<220> FEATURE:
<221> NAME/KEY: CDS
<222> LOCATION: (1)..(657)

<400> SEQUENCE: 42 atg tgc cca gca cct ccg gtg gcg gga ccg tca gtc ttc ctc ttc ccc     48
Met Cys Pro Ala Pro Pro Val Ala Gly Pro Ser Val Phe Leu Phe Pro
1               5                   10                  15 cca aaa ccc aag gac acc ctc atg atc tcc cgg acc cct gag gtc aca     96
Pro Lys Pro Lys Asp Thr Leu Met Ile Ser Arg Thr Pro Glu Val Thr
            20                  25                  30 tgc gtg gtg gtg gac gtg agc cac gaa gac cct gag gtc cag ttc aac    144
Cys Val Val Val Asp Val Ser His Glu Asp Pro Glu Val Gln Phe Asn
        35                  40                  45 tgg tac gtg gac ggc gtg gag gtg cat aat gcc aag aca aag ccg cgg    192
Trp Tyr Val Asp Gly Val Glu Val His Asn Ala Lys Thr Lys Pro Arg
    50                  55                  60 gag gag cag ttt aac agc acg ttt cgt gtg gtc agc gtc ctc acc gtc    240
Glu Glu Gln Phe Asn Ser Thr Phe Arg Val Val Ser Val Leu Thr Val
65                  70                  75                  80

```
gtg cac cag gac tgg ctg aat ggc aag gag tac aag tgc aag gtc tcc    288
Val His Gln Asp Trp Leu Asn Gly Lys Glu Tyr Lys Cys Lys Val Ser
             85                  90                  95 aac aaa ggc ctc cca gcc ccc atc gag aaa acc atc tcc aaa acc aaa    336
Asn Lys Gly Leu Pro Ala Pro Ile Glu Lys Thr Ile Ser Lys Thr Lys
        100                 105                 110 ggg cag ccc cga gag cca cag gtg tac acc ctg ccc cca tcc cgg gaa    384
Gly Gln Pro Arg Glu Pro Gln Val Tyr Thr Leu Pro Pro Ser Arg Glu
    115                 120                 125 gag atg acc aag aac cag gtc agc ctg acc tgc ctg gtc aaa ggc ttc    432
Glu Met Thr Lys Asn Gln Val Ser Leu Thr Cys Leu Val Lys Gly Phe
130                 135                 140 tat ccc agc gac atc gcc gtg gag tgg gag agc aat ggg cag ccg gag    480
Tyr Pro Ser Asp Ile Ala Val Glu Trp Glu Ser Asn Gly Gln Pro Glu
145                 150                 155                 160 aac aac tac aag acc acg cct ccc atg ctg gac tcc gac ggc tcc ttc    528
Asn Asn Tyr Lys Thr Thr Pro Pro Met Leu Asp Ser Asp Gly Ser Phe
                165                 170                 175 ttc ctc tac agc aag ctc acc gtg gac aag agc agg tgg cag cag ggg    576
Phe Leu Tyr Ser Lys Leu Thr Val Asp Lys Ser Arg Trp Gln Gln Gly
            180                 185                 190 aac gtc ttc tca tgc tcc gtg atg cat gag gct ctg cac aac cac tac    624
Asn Val Phe Ser Cys Ser Val Met His Glu Ala Leu His Asn His Tyr
        195                 200                 205 acg cag aag agc ctc tcc ctg tct ccg ggt aaa                        657
Thr Gln Lys Ser Leu Ser Leu Ser Pro Gly Lys
    210                 215

<210> SEQ ID NO 43
<211> LENGTH: 219
<212> TYPE: PRT
<213> ORGANISM: Homo sapiens

<400> SEQUENCE: 43

Met Cys Pro Ala Pro Val Ala Gly Pro Ser Val Phe Leu Phe Pro
1               5                   10                  15

Pro Lys Pro Lys Asp Thr Leu Met Ile Ser Arg Thr Pro Glu Val Thr
            20                  25                  30

Cys Val Val Val Asp Val Ser His Glu Asp Pro Glu Val Gln Phe Asn
        35                  40                  45

Trp Tyr Val Asp Gly Val Glu Val His Asn Ala Lys Thr Lys Pro Arg
    50                  55                  60

Glu Glu Gln Phe Asn Ser Thr Phe Arg Val Val Ser Val Leu Thr Val
65                  70                  75                  80

Val His Gln Asp Trp Leu Asn Gly Lys Glu Tyr Lys Cys Lys Val Ser
                85                  90                  95

Asn Lys Gly Leu Pro Ala Pro Ile Glu Lys Thr Ile Ser Lys Thr Lys
            100                 105                 110

Gly Gln Pro Arg Glu Pro Gln Val Tyr Thr Leu Pro Pro Ser Arg Glu
        115                 120                 125

Glu Met Thr Lys Asn Gln Val Ser Leu Thr Cys Leu Val Lys Gly Phe
    130                 135                 140

Tyr Pro Ser Asp Ile Ala Val Glu Trp Glu Ser Asn Gly Gln Pro Glu
145                 150                 155                 160

Asn Asn Tyr Lys Thr Thr Pro Pro Met Leu Asp Ser Asp Gly Ser Phe
                165                 170                 175

Phe Leu Tyr Ser Lys Leu Thr Val Asp Lys Ser Arg Trp Gln Gln Gly
            180                 185                 190
```

```
Asn Val Phe Ser Cys Ser Val Met His Glu Ala Leu His Asn His Tyr
        195                 200                 205
Thr Gln Lys Ser Leu Ser Leu Ser Pro Gly Lys
    210                 215
```

<210> SEQ ID NO 44
<211> LENGTH: 678
<212> TYPE: DNA
<213> ORGANISM: Homo sapiens
<220> FEATURE:
<221> NAME/KEY: CDS
<222> LOCATION: (1)..(678)

<400> SEQUENCE: 44

```
atg tgt tgt gtc gag tgc cca ccg tgc cca gca cct ccg gtg gcg gga         48
Met Cys Cys Val Glu Cys Pro Pro Cys Pro Ala Pro Pro Val Ala Gly
1               5                   10                  15 ccg tca gtc ttc ctc ttc ccc cca aaa ccc aag gac acc ctc atg atc         96
Pro Ser Val Phe Leu Phe Pro Pro Lys Pro Lys Asp Thr Leu Met Ile
            20                  25                  30 tcc cgg acc cct gag gtc aca tgc gtg gtg gtg gac gtg agc cac gaa        144
Ser Arg Thr Pro Glu Val Thr Cys Val Val Val Asp Val Ser His Glu
        35                  40                  45 gac cct gag gtc cag ttc aac tgg tac gtg gac ggc gtg gag gtg cat        192
Asp Pro Glu Val Gln Phe Asn Trp Tyr Val Asp Gly Val Glu Val His
    50                  55                  60 aat gcc aag aca aag ccg cgg gag gag cag ttt aac agc acg ttt cgt        240
Asn Ala Lys Thr Lys Pro Arg Glu Glu Gln Phe Asn Ser Thr Phe Arg
65                  70                  75                  80 gtg gtc agc gtc ctc acc gtc gtg cac cag gac tgg ctg aat ggc aag        288
Val Val Ser Val Leu Thr Val Val His Gln Asp Trp Leu Asn Gly Lys
                85                  90                  95 gag tac aag tgc aag gtc tcc aac aaa ggc ctc cca gcc ccc atc gag        336
Glu Tyr Lys Cys Lys Val Ser Asn Lys Gly Leu Pro Ala Pro Ile Glu
            100                 105                 110 aaa acc atc tcc aaa acc aaa ggg cag ccc cga gag cca cag gtg tac        384
Lys Thr Ile Ser Lys Thr Lys Gly Gln Pro Arg Glu Pro Gln Val Tyr
        115                 120                 125 acc ctg ccc cca tcc cgg gaa gag atg acc aag aac cag gtc agc ctg        432
Thr Leu Pro Pro Ser Arg Glu Glu Met Thr Lys Asn Gln Val Ser Leu
    130                 135                 140 acc tgc ctg gtc aaa ggc ttc tat ccc agc gac atc gcc gtg gag tgg        480
Thr Cys Leu Val Lys Gly Phe Tyr Pro Ser Asp Ile Ala Val Glu Trp
145                 150                 155                 160 gag agc aat ggg cag ccg gag aac aac tac aag acc acg cct ccc atg        528
Glu Ser Asn Gly Gln Pro Glu Asn Asn Tyr Lys Thr Thr Pro Pro Met
                165                 170                 175 ctg gac tcc gac ggc tcc ttc ttc ctc tac agc aag ctc acc gtg gac        576
Leu Asp Ser Asp Gly Ser Phe Phe Leu Tyr Ser Lys Leu Thr Val Asp
            180                 185                 190 aag agc agg tgg cag cag ggg aac gtc ttc tca tgc tcc gtg atg cat        624
Lys Ser Arg Trp Gln Gln Gly Asn Val Phe Ser Cys Ser Val Met His
        195                 200                 205 gag gct ctg cac aac cac tac acg cag aag agc ctc tcc ctg tct ccg        672
Glu Ala Leu His Asn His Tyr Thr Gln Lys Ser Leu Ser Leu Ser Pro
    210                 215                 220 ggt aaa                                                                678
Gly Lys
225
```

<210> SEQ ID NO 45

<211> LENGTH: 226
<212> TYPE: PRT
<213> ORGANISM: Homo sapiens

<400> SEQUENCE: 45

Met Cys Cys Val Glu Cys Pro Pro Cys Pro Ala Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Gln Phe Asn Trp Tyr Val Asp Gly Val Glu Val His
    50                  55                  60

Asn Ala Lys Thr Lys Pro Arg Glu Glu Gln Phe Asn Ser Thr Phe Arg
65                  70                  75                  80

Val Val Ser Val Leu Thr Val Val His Gln Asp Trp Leu Asn Gly Lys
                85                  90                  95

Glu Tyr Lys Cys Lys Val Ser Asn Lys Gly Leu Pro Ala Pro Ile Glu
            100                 105                 110

Lys Thr Ile Ser Lys Thr Lys Gly Gln Pro Arg Glu Pro Gln Val Tyr
        115                 120                 125

Thr Leu Pro Pro Ser Arg Glu Glu Met Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Met
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 46
<211> LENGTH: 675
<212> TYPE: DNA
<213> ORGANISM: Homo sapiens
<220> FEATURE:
<221> NAME/KEY: CDS
<222> LOCATION: (1)..(675)

<400> SEQUENCE: 46 atg tgt gtc gag tgc cca ccg tgc cca gca cct ccg gtg gcg gga ccg      48
Met Cys Val Glu Cys Pro Pro Cys Pro Ala Pro Val Ala Gly Pro
1               5                   10                  15 tca gtc ttc ctc ttc ccc cca aaa ccc aag gac acc ctc atg atc tcc      96
Ser Val Phe Leu Phe Pro Pro Lys Pro Lys Asp Thr Leu Met Ile Ser
            20                  25                  30 cgg acc cct gag gtc aca tgc gtg gtg gtg gac gtg agc cac gaa gac     144
Arg Thr Pro Glu Val Thr Cys Val Val Val Asp Val Ser His Glu Asp
        35                  40                  45 cct gag gtc cag ttc aac tgg tac gtg gac ggc gtg gag gtg cat aat     192
Pro Glu Val Gln Phe Asn Trp Tyr Val Asp Gly Val Glu Val His Asn
    50                  55                  60 gcc aag aca aag ccg cgg gag gag cag ttt aac agc acg ttt cgt gtg     240
Ala Lys Thr Lys Pro Arg Glu Glu Gln Phe Asn Ser Thr Phe Arg Val

```
gtc agc gtc ctc acc gtc gtg cac cag gac tgg ctg aat ggc aag gag    288
Val Ser Val Leu Thr Val Val His Gln Asp Trp Leu Asn Gly Lys Glu
                85                  90                  95 tac aag tgc aag gtc tcc aac aaa ggc ctc cca gcc ccc atc gag aaa    336
Tyr Lys Cys Lys Val Ser Asn Lys Gly Leu Pro Ala Pro Ile Glu Lys
            100                 105                 110 acc atc tcc aaa acc aaa ggg cag ccc cga gag cca cag gtg tac acc    384
Thr Ile Ser Lys Thr Lys Gly Gln Pro Arg Glu Pro Gln Val Tyr Thr
        115                 120                 125 ctg ccc cca tcc cgg gaa gag atg acc aag aac cag gtc agc ctg acc    432
Leu Pro Pro Ser Arg Glu Glu Met Thr Lys Asn Gln Val Ser Leu Thr
    130                 135                 140 tgc ctg gtc aaa ggc ttc tat ccc agc gac atc gcc gtg gag tgg gag    480
Cys Leu Val Lys Gly Phe Tyr Pro Ser Asp Ile Ala Val Glu Trp Glu
145                 150                 155                 160 agc aat ggg cag ccg gag aac aac tac aag acc acg cct ccc atg ctg    528
Ser Asn Gly Gln Pro Glu Asn Asn Tyr Lys Thr Thr Pro Pro Met Leu
                165                 170                 175 gac tcc gac ggc tcc ttc ttc ctc tac agc aag ctc acc gtg gac aag    576
Asp Ser Asp Gly Ser Phe Phe Leu Tyr Ser Lys Leu Thr Val Asp Lys
            180                 185                 190 agc agg tgg cag cag ggg aac gtc ttc tca tgc tcc gtg atg cat gag    624
Ser Arg Trp Gln Gln Gly Asn Val Phe Ser Cys Ser Val Met His Glu
        195                 200                 205 gct ctg cac aac cac tac acg cag aag agc ctc tcc ctg tct ccg ggt    672
Ala Leu His Asn His Tyr Thr Gln Lys Ser Leu Ser Leu Ser Pro Gly
    210                 215                 220 aaa                                                                 675
Lys
225

<210> SEQ ID NO 47
<211> LENGTH: 225
<212> TYPE: PRT
<213> ORGANISM: Homo sapiens

<400> SEQUENCE: 47

Met Cys Val Glu Cys Pro Pro Cys Pro Ala Pro Pro Val Ala Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Gln Phe Asn Trp Tyr Val Asp Gly Val Glu Val His Asn
    50                  55                  60

Ala Lys Thr Lys Pro Arg Glu Glu Gln Phe Asn Ser Thr Phe Arg Val
65                  70                  75                  80

Val Ser Val Leu Thr Val Val His Gln Asp Trp Leu Asn Gly Lys Glu
                85                  90                  95

Tyr Lys Cys Lys Val Ser Asn Lys Gly Leu Pro Ala Pro Ile Glu Lys
            100                 105                 110

Thr Ile Ser Lys Thr Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160
```

Ser Asn Gly Gln Pro Glu Asn Tyr Lys Thr Thr Pro Pro Met Leu
            165                 170                 175

Asp Ser Asp Gly Ser Phe Phe Leu Tyr Ser Lys Leu Thr Val Asp Lys
        180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
    210                 215                 220

Lys
225

<210> SEQ ID NO 48
<211> LENGTH: 3
<212> TYPE: PRT
<213> ORGANISM: Homo sapiens

<400> SEQUENCE: 48

Glu Pro Lys
1

<210> SEQ ID NO 49
<211> LENGTH: 3
<212> TYPE: PRT
<213> ORGANISM: Homo sapiens

<400> SEQUENCE: 49

Ser Cys Asp
1

<210> SEQ ID NO 50
<211> LENGTH: 3
<212> TYPE: PRT
<213> ORGANISM: Homo sapiens

<400> SEQUENCE: 50

Asp Lys Thr
1

<210> SEQ ID NO 51
<211> LENGTH: 2
<212> TYPE: PRT
<213> ORGANISM: Homo sapiens

<400> SEQUENCE: 51

Cys Pro
1

<210> SEQ ID NO 52
<211> LENGTH: 3
<212> TYPE: PRT
<213> ORGANISM: Homo sapiens

<400> SEQUENCE: 52

Pro Lys Ser
1

<210> SEQ ID NO 53
<211> LENGTH: 3
<212> TYPE: PRT
<213> ORGANISM: Homo sapiens

<400> SEQUENCE: 53

Cys Pro Pro
1

```
<210> SEQ ID NO 54
<211> LENGTH: 3
<212> TYPE: PRT
<213> ORGANISM: Homo sapiens

<400> SEQUENCE: 54

Pro Pro Cys
1

<210> SEQ ID NO 55
<211> LENGTH: 3
<212> TYPE: PRT
<213> ORGANISM: Homo sapiens

<400> SEQUENCE: 55

Pro Cys Pro
1

<210> SEQ ID NO 56
<211> LENGTH: 3
<212> TYPE: PRT
<213> ORGANISM: Homo sapiens

<400> SEQUENCE: 56

Pro Pro Cys
1

<210> SEQ ID NO 57
<211> LENGTH: 3
<212> TYPE: PRT
<213> ORGANISM: Homo sapiens

<400> SEQUENCE: 57

Pro Cys Pro
1

<210> SEQ ID NO 58
<211> LENGTH: 2
<212> TYPE: PRT
<213> ORGANISM: Homo sapiens

<400> SEQUENCE: 58

Cys Pro
1

<210> SEQ ID NO 59
<211> LENGTH: 9
<212> TYPE: PRT
<213> ORGANISM: Homo sapiens

<400> SEQUENCE: 59

Cys Cys Val Glu Cys Pro Pro Cys Pro
1               5

<210> SEQ ID NO 60
<211> LENGTH: 8
<212> TYPE: PRT
<213> ORGANISM: Homo sapiens

<400> SEQUENCE: 60

Cys Val Glu Cys Pro Pro Cys Pro
1               5

<210> SEQ ID NO 61
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Met Ser Cys Pro
1

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Met Pro Ser Cys Pro
1               5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Met Cys Pro Ser Cys Pro
1               5

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Met Glu Pro Lys
1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Met Ser Cys Asp
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Met Asp Lys Thr
```

```
<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Met Cys Pro Ala
1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Pro Lys Ser
1

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Met Cys Pro Pro
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Met Pro Pro Cys
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Met Pro Cys Pro
1

<210> SEQ ID NO 72
<211> LENGTH: 40
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 72
ggaattccat atggagccca aatcttgtga caaaactcac                                40

<210> SEQ ID NO 73
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggaattccat atgtcttgtg acaaaactca cacatgccc                                 39

<210> SEQ ID NO 74
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggaattccat atggacaaaa ctcacacatg cccaccgtgc                                40

<210> SEQ ID NO 75
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gggaattcca tatgtgccca gcacctgaac tcctgggg                                  38

<210> SEQ ID NO 76
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gggaattcca tatgcccaaa tcttgtgaca aaactcac                                  38

<210> SEQ ID NO 77
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gggaattcca tatgtgccca ccgtgcccag cacctgaact cc                             42

<210> SEQ ID NO 78
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ggaattccat atgccaccgt gcccagcacc tgaactcctg                40

<210> SEQ ID NO 79
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
ggaattccat atgccgtgcc cagcacctga actcctgggg                40

<210> SEQ ID NO 80
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
cgcggatcct catttacccg gagacaggga gaggctcttc                40

<210> SEQ ID NO 81
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gggaattcca tatgccaccg tgcccagcac cacctgtggc agg            43

<210> SEQ ID NO 82
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gggaattcca tatgccgtgc ccagcaccac ctgtggcagg ac             42

<210> SEQ ID NO 83
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gggaattcca tatgtgccca gcaccacctg tggcaggac                 39

<210> SEQ ID NO 84
<211> LENGTH: 43
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 84
gggaattcca tatgtgttgt gtcgagtgcc caccgtgccc agc                43

<210> SEQ ID NO 85
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gggaattcca tatgtgtgtc gagtgcccac cgtgcccagc acc                43

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Met Cys Cys Val Glu Cys Pro Pro Cys Pro
1               5                   10

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Met Cys Val Glu Cys Pro Pro Cys Pro
1               5
```

METHOD FOR THE MASS PRODUCTION OF IMMUNOGLOBULIN FC REGION DELETED INITIAL METHIONINE RESIDUES

CROSS-REFERENCE TO RELATED APPLICATION

This application is a 371 National Stage entry of International Application No. PCT/KR2006/003207, filed Aug. 16, 2006, now WO/2007/021129 publication date Feb. 22, 2007, the entire specification, claims, drawings and sequence listing of which are incorporated herewith by reference.

TECHNICAL FIELD

The present invention relates to a method for producing a monomeric or dimeric immunoglobulin Fc region free of initial methionine residues on a mass scale by taking advantage of a recombinant expression vector comprising a nucleotide sequence coding for a recombinant immunoglobulin Fc region including an immunoglobulin hinge region.

BACKGROUND ART

With advances in genetic engineering, a large number of protein drugs have been developed and utilized. Susceptible to denaturation or proteolytic degradation in the body, protein drugs, however, are difficult to keep at in vivo concentrations and titers for a long period of time. An improvement in protein stability in vivo, which can lead to the maintenance of in vivo concentrations of protein drugs at suitable levels is important not only in promoting the efficacy of therapy, but also in helping patients who need to take frequent injections of their protein drugs, in terms of convenience and cost.

Many attempts have been made to enhance the in vivo stability of protein drugs for a long time, exemplified by changing the protein formulation, fusing a protein to another protein, or chemically or biologically attaching a suitable polymer to the surface of a protein.

One of such technique is making a fusion protein with the immunoglobulin Fc fragment.

The Fc fragment mediates effector functions such as complement-dependent cytotoxicity (CDC) or antibody-dependent cell-mediated cytotoxicity (ADCC), as well as antigen binding capacity, which is the unique function of immunoglobulins. Also, the Fc fragment contains a sequence participating in the binding to the neonatal Fc receptor (FcRn), which plays a role in regulating serum IgG levels by increasing the transport of maternal IgG to neonates and the half-life of the IgG (Ghetie and Ward, *Immunology Today* 18: 592-598, 1997), and the sequence regulates the interaction between protein A and protein G. Through the fusion of this Fc fragment with a therapeutic protein, many studies have been performed to enhance the stability of the therapeutic protein.

For example, Korean Pat. No. 249572 discloses a fusion protein which is prepared by linking an IgG1 heavy chain Fc region (Fc) at an amino terminal end thereof to a carboxyl terminal end of a protein, such as an IL4 receptor, an IL7 receptor, a G-CSF receptor or an EPO receptor, and producing the resulting fusion protein in mammalian cells. U.S. Pat. No. 5,605,690 describes a fusion protein comprising a tumor necrosis factor receptor fused at its carboxyl terminal end to a human IgG1 Fc derivative, the fusion protein being produced in animal cells. Also, Tanox Inc. reported, in U.S. Pat. Nos. 5,723,125 and 5,908,626, a hybrid molecule comprising human interferon alpha or beta that is linked at its carboxyl terminal end to native human IgG4 Fc through a peptide linker, and produced in animal cells. Lexigen Inc., as described in International PCT Application Publication No. WO 00/69913, prepared a native IgG1 Fc linked at its carboxyl terminal end to the amino terminal end of human interferon by genetic recombination without the use of a linker and produced the fusion protein in animal cells. U.S. Pat. Publication No. 20030082679 discloses a fusion protein with an extended serum half-life, which comprises human G-CSF linked at its carboxyl terminal end to the amino terminal end of IgG1 Fc and is produced in animal cells. U.S. Pat. Publication No. 20010053539, U.S. Pat. No. 6,030,613, International PCT Application Publication Nos. WO 99/02709 and WO 01/03737 and European Pat. No. 0464533B1 disclose an Fc fusion protein with a longer serum half-life than a native protein, which comprises an IgG1 Fc or Fc derivative linked at its amino terminal end through a peptide linker or without a peptide linker to the carboxyl terminal end of human EPO, TPO, human growth hormone or human interferon beta, the Fc fusion protein being produced in animal cells.

These Fc fusion proteins, as described above, increase the serum half-life of target proteins, but entail problems related to the mediation of effector functions by the Fc fragment (U.S. Pat. No. 5,349,053). Through the effector functions of the Fc fragment, they fix complements or bind to cells expressing FcγRs, leading to lysis of specific cells, and induce the production and secretion of several cytokines inducing inflammation, leading to unwanted inflammation. Also, the fusion creates a new amino acid sequence at a connection region between the Fc fragment and the protein partner, which could potentially induce immune responses if administered for a long time.

In this regard, many efforts have been made to prepare an immunoglobulin or immunoglobulin fragment that has a long serum half-life but is deficient in effector functions. Cole et al. reported that, when amino acid residues of the CH2 region at positions 234, 235 and 237, known to play an important role in binding to Fc receptors, are replaced with alanine to thus produce an Fc derivative having a reduced binding affinity to Fc receptors, the ADCC activity is inhibited (Cole et al., *J. Immunol.* 159: 3613-3621, 1997). However, in all of these variants, Fc may have increased immunogenicity or antigenicity compared to the native human Fc fragment due to the presence of unsuitable amino acids, and may lose desirable Fc functions.

Among methods of deleting or reducing undesirable effector functions while maintaining high serum concentrations of an immunoglobulin, one is based on removing sugar moieties from the immunoglobulin. As described in U.S. Pat. No. 5,585,097, an aglycosylated antibody derivative as an anti-CD3 antibody can be prepared by replacing a glycosylated residue of antibodies, the asparagine residue at position 297 of the CH2 domain, with another amino acid. This aglycosylated antibody derivative exhibits reduced effector functions, but still retains its binding affinity to FcRn receptor, with no change in serum half-life. However, this derivative is also problematic in terms of being potentially recognized as a foreign material and rejected by the immune system due to the production of a novel recombinant construct having an abnormal sequence. U.S. Pat. Publication No. 20030073164 discloses a method of producing an Fc derivative using *E. coli* devoid of glycosylation ability so as to prepare a therapeutic antibody deficient in effector functions.

The American company Amgen Inc. described, in U.S. Pat. No. 6,660,843 and U.S. Pat. Publication Nos. 20040044188 and 20040053845, a human IgG1 Fc derivative having amino acid deletions at the first five amino acid residues of the hinge region, which is fused to the amino or carboxyl terminal end of a therapeutic protein or a therapeutic protein mimicked by a peptide, and the production thereof using an *E. coli* host. However, this fusion protein not having a signal sequence is expressed as inclusion bodies, and thus must be subjected to an additional refolding process. This protein refolding process reduces yields, and, especially in a protein present as a homodimer or a heterodimer, remarkably reduces dimer production. Also, when a protein not having a signal sequence is expressed in *E. coli*, a methionine residue is added to the N-terminus of the expression product due to the feature of the protein expression system of *E. coli*. The aforementioned expression products of Amgen Inc. have an N-terminal methionine residue, which may induce immune responses upon repeated or excessive administration to the body. Also, since these fusion molecules are expressed in a fusion protein form in *E. coli* by linking a gene encoding a therapeutic protein to an Fc gene, they are difficult to express in *E. coli*, or a therapeutic protein is difficult to produce in *E. coli* if its expression in *E. coli* in a fused form results in a significant decrease or loss of activity. Further, since the fusion of two molecules creates a non-naturally occurring abnormal amino acid sequence at the connection region between two proteins, the fusion protein could potentially be recognized as "non-self" by the immune system, and thus induce immune responses.

To solve these problems, the present inventors previously prepared an Fc fragment and a protein drug as separate polypeptides, not using a fusion method based on genetic recombination but using the best expression systems, and covalently linking the two polypeptides together to use the Fc fragment as a drug carrier. In this case, it is possible to prepare a conjugate of a glycosylated polypeptide drug and an aglycosylated Fc, which does not induce undesirable immune responses but has satisfactory properties of physiological drug activity, in vivo duration and stability.

In the above case, since it is preferable that the Fc is in an aglycosylated form, a prokaryotic expression system such as *E. coli* is used. Protein production methods using an *E. coli* expression system have several advantages over conventional methods using animal cells, as follows. An *E. coli* expression vector can be easily constructed, thus allowing rapid evaluation of protein expression. Due to its rapid growth rate, *E. coli* allows mass production of a protein of interest at low cost. Also, a relatively simple expression process can be used. Thus, *E. coli* is more useful for commercial production than other host cells.

Most Fc regions are present as inclusion bodies upon overexpression in *E. coli*. For this reason, industry demands that Fc regions be expressed in water-soluble form in *E. coli*. European Pat. No. 0227110 discloses the production of the immunoglobulin G1 Fc region using only the product (the cell lysate) which is expressed in water soluble form upon the overexpression of the immunoglobulin G1 Fc region. However, only the immunoglobulin expressed in water-soluble form is as low as 15 mg/L in yield, which has no value in terms of industrial usefulness. Korean Pat. Appl'n No. 0092783, overcoming the problem encountered in the prior art, introduces a novel technique of expressing an immunoglobulin Fc region not as inclusion bodies but in a water-soluble form in *E. coli* through the fusion of the nucleotide sequence corresponding to the Fc region to an *E. coli* signal sequence. Upon expression in *E. coli*, the protein of interest is present a soluble form devoid of the signal peptide with the production yield thereof increased to as much as 600 mg/L.

Leading to the present invention, intensive and thorough research into a method of producing active aglycosylated immunoglobulin Fc regions free of immune response, conducted by the present inventors, aiming to increase the production yield to a level suitable for industrialization, resulted in the finding that when a nucleotide sequence encoding an immunoglobulin Fc region is expressed in a form fused at the N terminus to a specific hinge region, the immunoglobulin Fc region is expressed as inclusion bodies which are finally a dimer or a monomer of immbunoglobulin Fc region devoid of initial methionine residues through solubilization and refolding processes.

DISCLOSURE OF THE INVENTION

It is therefore an object of the present invention to provide a method of mass-producing an immunoglobulin Fc region free of initial methionine residue, comprising constructing a vector including a nucleotide sequence coding for a recombinant immunoglobulin Fc region containing an immunoglobulin hinge region; transforming a prokaryotic cell with the vector; culturing a resulting transformant; and isolating and purifying the immunoglobulin Fc region expressed in an inclusion body from the transformant.

It is another object of the present invention to provide a dimer or a monomer of an immunoglobulin Fc region prepared by the above method.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
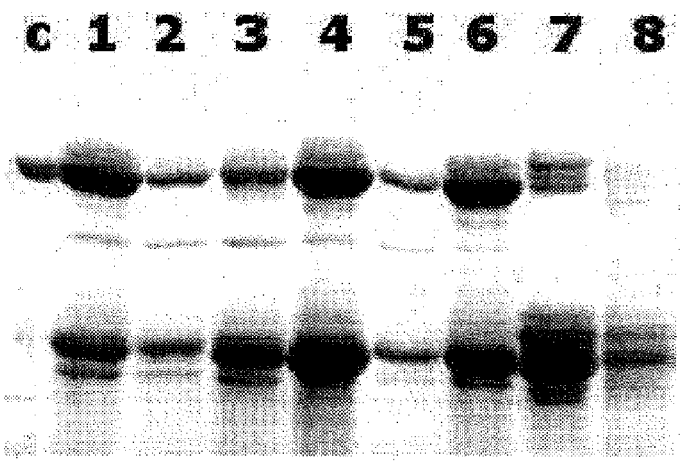
FIG. 1 is an electrophoresis gel photograph showing the formation of monomeric and dimeric Fc region fragments from inclusion bodies expressed using an expression vector having a nucleotide encoding a human immunoglobulin IgG4 Fc region.

In one aspect, the present invention relates to a method of mass-producing an immunoglobulin Fc region, comprising constructing a vector including a nucleotide sequence coding for a recombinant immunoglobulin Fc region containing an immunoglobulin hinge region; transforming a prokaryotic cell with the vector; culturing the resulting transformant; and isolating and purifying the immunoglobulin Fc region, expressed in an inclusion body form, from the transformant.

The present invention pertains to a method of mass-producing an immunoglobulin Fc region useful as a carrier for protein drugs. When an immunoglobulin Fc region is fused at the N terminus to a hinge region, the resulting recombinant immunoglobulin Fc region is found to be expressed as an inclusion body and then be solubilized and refolded into a dimer or monomer in an active form devoid of the initial methionine residue encoded by the initiation codon. The present invention is of great significance in terms of the finding that, when fused to an immunoglobulin Fc region, a hinge region plays a critical role in processing and refolding the recombinant Fc region into a native sequence form devoid of the initial methionine residue encoded by the initiation codon.

The hinge region capable of allowing an immunoglobulin Fc region to be mass produced in a recombinant form therewith may be a derivative from IgG, IgA, IgM, IgE or IgD of humans and other animals, including goats, swine, mice, rabbits, hamsters, rats and guinea pigs, with preference for a derivative of IgG, e.g., IgG1, IgG2, IgG3, or IgG4 (SEQ. ID. NOS. 14 to 17). The hinge region useful in the present invention may be a full-length hinge region or a fragment thereof. Preferable is a hinge region fragment having two or more consecutive amino acid sequences, which are more preferable when containing at least one cystein residue therein. Of practical use in the present invention are fragments of the hinge region derived from IgG4 of SEQ. ID. NO. 17, which are represented by SEQ. ID. NOS. 18, 19, 20 and 21. When hinge regions of SEQ. ID. NOS. 18, 19 and 20 are employed, the immunoglobulin Fc region can be prepared in a dimer or monomer form. The hinge region of SEQ. ID. NO. 21 effectively affords the preparation of a monomer of the immunoglobulin Fc region. In other implementations of the present invention, fragments, represented by SEQ. ID. NOS. 48 to 55, of the hinge region derived from IgG1 of SEQ. ID. NO. 14 and, represented by SEQ. ID. NOS. 56 to 60, of the hinge region derived from IgG2 of SEQ. ID. NO. 15 were used to produce a dimer of the immunoglobulin Fc region.

The immunoglobulin Fc region capable of being produced by the present invention may be a native form isolated from humans and other animals including goats, swine, mice, rabbits, hamsters, rats and guinea pigs, or may be a recombinant or a derivative thereof, obtained from transformed animal cells or microorganisms. Preferred may be an Fc region of IgG, IgA, IgM, IgE and IgD from humans, or a combination or hybrid thereof. The term "combination", as used herein, means that polypeptides encoding single-chain immunoglobulin Fc fragments of the same origin are linked to a single-chain polypeptide of a different origin to form a dimer or multimer. The term "hybrid", as used herein, means that sequences encoding two or more immunoglobulin Fc fragments of different origins are present in a single-chain immunoglobulin Fc fragment. The immunoglobulin may preferably be an Fc region of IgG1, IgG2, IgG3 and IgG4, or a combination or hybrid thereof. Nucleotide sequences encoding human immunoglobulin Fc regions and amino acid sequences limited to the same, useful in the present invention, may be those encoded by nucleotide sequences from the GenBank and/or EMBL databases.

The immunoglobulin Fc region of the present invention includes an amino acid sequence derivative. The term "amino acid sequence derivative" means a sequence in which one or more amino acid residues differ from a wild-type amino acid sequence, and may naturally occur or be artificially generated. The immunoglobulin Fc region includes derivatives resulting from a deletion, an insertion, a non-conservative or conservative substitution or combinations thereof. An insertion is typically made by the addition of a consecutive amino acid sequence of about 1 to 20 amino acids, or may be made with a longer sequence. A deletion is typically in the range of about 1 to 30 amino acid residues. Amino acid exchanges in proteins and peptides, which do not generally alter the activity of the proteins or peptides, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions. Such derivatives may be prepared through a chemical peptide synthesis method or a DNA sequence-based recombination method, which are known in the art (Sambrook et al., Molecular Cloning, Cold Spring Harbor Laboratory Press, New York, USA, 2d Ed., 1989).

In addition, the immunoglobulin Fc region, if desired, may be modified through phosphorylation, sulfation, acrylation, glycosylation, methylation, farnesylation, acetylation, amidation, and the like.

The immunoglobulin derivative of the present invention is preferably a functional equivalent to its natural form, thus having a similar biological activity, or, if desired, could be made by altering the property of the natural form. Preferably, the derivatives of the immunoglobulin Fc region are proteins that have increased structural stability against heat, pH, etc., or solubility, or that have improved characteristics in terms of disulfide bond formation, compatibility with an expression host, complement binding, Fc receptor binding and antibody-dependent cell-mediated cytotoxicity (ADCC), so long as the derivatives produced are not so different from natural forms of humans that they induce unwanted immune responses in humans and animals. Preferred derivatives are IgG1 Fc regions which are altered in such a specific residue as to have reduced affinity to Fc receptors mediating antibody-dependent cell-mediated cytotoxicity (ADCC). A derivative produced may contain a deletion or a substitution with another amino acid in the leucine residue at position 234 of an IgG1 CH2 sequence (see the sequence from the Kobat database for the numbering of the amino acid residues). Most preferably, Leu234 is replaced by phenylalanine, an amino acid residue at a corresponding position in IgG4.

In accordance with the present invention, a nucleotide sequence coding for a recombinant immunoglobulin Fc region in which an immunoglobulin Fc region is fused to an immunoglobulin hinge region is prepared. As used herein, the term "recombinant immunoglobulin Fc region" means an immunoglobulin Fc region linked at the N terminus to a hinge region via a peptide bond.

Depending on the immunoglobulin Fc region, the hinge region to be fused may be chosen. Preferable is a hinge region which is the same in origin as the immunoglobulin Fc region. In the actual practice of the present invention, a nucleotide sequence coding for a recombinant immunoglobulin Fc region consisting of an amino acid sequence set forth as SEQ. ID. NOS. 7, 9, 11 or 13, in which an IgG4-derived Fc region is fused to a hinge region consisting of an amino acid sequence set forth as SEQ. ID. NOS. 18, 19, 20 or 21, was prepared. The nucleotide sequences coding for the recombinant immunoglobulin Fc regions are represented by SEQ. ID. NOS. 6, 8, 10 and 12, respectively.

In another implementation, prepared was a nucleotide sequence coding for a recombinant immunoglobulin Fc region consisting of an amino acid sequence set forth as in SEQ. ID. NO. 23, 25, 27, 29, 31, 33, 35 or 37, in which an IgG1-derived Fc region is fused to a hinge region consisting of an amino acid sequence set forth as one of SEQ. ID. NOS. 48 to 55. The resulting nucleotide sequences encoding the recombinant immunoglobulin Fc regions are represented by SEQ. ID. NOS. 22, 24, 26, 28, 30, 32, 34 and 36.

In a further implementation, prepared was a nucleotide sequence coding for a recombinant immunoglobulin Fc region consisting of an amino acid sequence set forth as in SEQ. ID. NO. 39, 41, 43, 45 or 47, in which an IgG2-derived Fc region is fused to a hinge region consisting of an amino acid sequence set forth as one of SEQ. ID. NOS. 56 to 60. The resulting nucleotide sequences encoding the recombinant immunoglobulin Fc regions are represented by SEQ. ID. NOS. 38, 40, 42, 44 and 46.

In accordance with the present invention, recombinant expression vectors to which nucleotide sequences encoding the recombinants immunoglobulin Fc regions are operably linked are provided.

The term "recombinant expression vector", as used herein, which describes a vector capable of expressing a target protein in a suitable host cell, refers to a genetic construct that comprises essential regulatory elements to which a gene insert is operably linked in such a manner as to be expressed in a host cell.

The term "operably linked", as used herein, refers to a functional linkage between a nucleic acid expression control sequence and a second nucleic acid sequence coding for a target protein in such a manner as to allow general functions. The operable linkage to a recombinant vector may be prepared using a genetic recombinant technique well known in the art, and site-specific DNA cleavage and ligation may be carried out using enzymes generally known in the art. A suitable expression vector includes expression regulatory elements, such as a promoter, an initiation codon, a stop codon, a polyadenylation signal and an enhancer. The initiation and stop codons are necessary for functionality in an individual to whom a genetic construct has been administered, and must be in frame with the coding sequence. The promoter of the vector may be constitutive or inducible. In addition, expression vectors include a selectable marker that allows selection of host cells containing the vector, and replicable expression vectors include a replication origin. In the detailed practice of the present invention, the following recombinant expression vectors are prepared: pmSCPFc, pmPSCFc, pmCPSFc, pmCPFc, pMEPKFC1, pMSCKFc1, pMDKTFc1, pMCPAFc1, pMPKSFc1, pMCPPFc1, pMPPCFc, pMPCPFc, pmPPCG2Fc, pmPCPG2Fc, pmCPG2Fc, pmCCVG2Fc and pmCVE2Fc.

The recombinant expression vectors expressing the proteins are transformed into host cells.

With respect to the object of the present invention, the host cells are prokaryotic cells in which glycosylation does not occur. Examples of these prokaryotic cells include *Escherichia coli, Bacillus subtilis, Streptomyces, Pseudomonas, Proteus mirabilis* and *Staphylococcus*, with preference for *E. coli*. Illustrating, non-limiting examples of *E. coli* strains include BL21 (DE3), JM109, DH series, TOP10 and HB101. More preferable is the BL21 (DE3) strain. Because it lacks a system for protein glycosylation, *E. coli* can be used as a host cell in which an immunoglobulin Fc region is produced in the form of being devoid of sugar moieties that are present in a CH2 domain of a native immunoglobulin. Sugar moieties of the immunoglobulin CH2 domain do not affect the structural stability of immunoglobulins, but cause immunoglobulins to mediate antibody-dependent cell-mediated cytotoxicity (ADCC) upon association with cells expressing Fc receptors and immune cells, in order to secrete cytokines to induce inflammation. Also, the sugar moieties bind to the C1q part of the first complement component C1, leading to complement fixation. Thus, when an immunoglobulin Fc region is produced in an aglycosylated form and linked to a therapeutic protein, the therapeutic protein is present in the serum for a prolonged period of time without the undesirable effector functions of immunoglobulins.

The transformation of the recombinant expression vectors into prokaryotic cells can be achieved by any method that allows nucleic acids to be introduced into cells and, as known in the art, may be performed by selecting suitable standard techniques according to host cells. These methods include, but are not limited to, electroporation, protoplast fusion, calcium phosphate ($CaPO_4$) precipitation, calcium chloride ($CaCl_2$) precipitation, agitation with silicon carbide fiber, and PEG-, dextran sulfate- and lipofectamine-mediated transformation.

In the detailed practice of the present invention, the recombinant expression vectors are individually introduced into *E. coli*, thus generating the following transformants: BL21/pmSCPFc (HM11200), BL21/pmPSCFc (HM11201), BL21/pmCPSFc (HM11204), BL21/pmCPAFc (HM11205), BL21/pMEPKFc1 (HM11206), BL21/pMSCDFc1 (HM11207), BL21/pMDKTFc1 (HM11208), BL21/pMCPAFc1 (HM11209), BL21/pMPKSFc1 (HM11210), BL21/pMCPPFc1 (HM11211), BL21/pMPPCFc1 (HM11212), BL21/pMPCPFc1 (HM11213), BL21/pmPPCPG2Fc (HM11214), BL21/pmPCPG2Fc (HM11215), BL21/pmCPG2Fc (HM11216) and BL21/pmCCvG2Fc (HM11217), BL21/pmCVEG2Fc (HM11218).

The transformants anchoring the recombinant expression vectors thereat are cultured through a general method.

Culture conditions may be easily adjusted according to bacterial strain by those skilled in the art. Typically, the medium used for the culture should contain all nutrients essential for the growth and survival of cells. The medium should contain a variety of carbon sources, nitrogen sources and trace elements. Examples of available carbon sources include glucose, sucrose, lactose, fructose, maltose, starch, carbohydrates such as cellulose, fats such as soybean oil, sunflower oil, castor oil and coconut oil, fatty acids such as palmitic acid, stearic acid and linoleic acid, alcohols such as glycerol and ethanol, and organic acids such as acetic acid. These carbon sources may be used singly or in combinations of two or more. Examples of available nitrogen sources include organic nitrogen sources, such as peptone, yeast extract, meat extract, malt extract, corn steep liquor (CSL) and soybean whey, and inorganic nitrogen sources, such as urea, ammonium sulfate, ammonium chloride, ammonium phosphate, ammonium carbonate and ammonium nitrate. These nitrogen sources may be used singly or in combinations of two or more. A phosphorus source may be contained in the medium, which includes potassium dihydrogen phosphate, dipotassium hydrogen phosphate and corresponding sodium-containing salts. In addition, the medium may contain a metal salt, such as magnesium sulfate or iron sulfate. The medium may further include amino acids, vitamins, suitable precursors, and the like. The pH of the culture may be adjusted by adding a compound, such as ammonium hydroxide, potassium hydroxide, ammonia, phosphoric acid and sulfuric acid, to the culture using a suitable method. Also, during the culture, antifoaming agents, such as polyglycol fatty acid esters, may be used to prevent bubble formation. To maintain the culture in a desirable state, oxygen or an oxygen-containing gas (e.g., air) is introduced into the culture. The temperature of the culture is generally 20° C. to 45° C., and preferably 25° C. to 45° C. Also, a fermentor can be used for protein production on a large scale. Protein production using a fermentor should be carried out taking into consideration several factors, including the growth rate of host cells and protein expression levels. Protein expression may be induced through adding, for example, IPTG to the medium under suitable culture conditions.

An immunoglobulin Fc region overexpressed as inclusion bodies may be purified through a general technique. The immunoglobulin Fc regions produced in the transformants may be obtained by disrupting cells using a French press, an ultrasonicator, etc., collecting only water-insoluble inclusion bodies containing the immunoglobulin Fc region through centrifugation, solubilizing and denaturing the collected fraction with refolding agents, such as urea, guanidine, arginine, cystein, beta-mercaptoethanol, etc. to the refolding thereof, and purifying the refolded fusion protein through dialysis, various chromatographies, such as gel filtration, ion exchange and reverse phase column chromatography, and ultrafiltration, alone or in combination. Generally, this refolding process is very complicated and is known to produce a very low refolding yield and assure the refolded protein only of lower activity than that of the water-soluble protein.

However, the method of the present invention can overcome the above-mentioned problems and produce an active immunoglobulin Fc region devoid of the initial methionine residue on a mass scale. On the whole, when expressed and produced in $E.$ $coli$, an exogenous protein has an initial methionine residue encoded by the initiation codon. Repetitive or excessive administration of the protein product having the initial methionine to human bodies may cause an immune response sufficient to reduce the therapeutic effect thereof or to be toxic. However, when the recombinant immunoglobulin Fc region of the present invention is expressed in $E.$ $coli$, the initial methionine residue is found to be cleaved by aminopeptidase, an intrinsic cytoplasmic enzyme, as measured by N-terminal sequencing analysis (Adams et al., J. Mol. Biol. 33:571-589, 1968, Takeda, Proc. Natl. Acad. Sci. USA 60:1487-1494, 1968). The activity of such aminopeptidases is known to depend on the sequence and structure of the protein of interest (Moerschell et al., J. Biol. Chem. 265:19638-19643, 1990, James et al., Protein Expression and Purification 41:45-52, 2005). A hinge region, when fused to an immunoglobulin Fc region, is affected by aminopeptidase so that the initial methionine is processed to an extent that depends on the amino acid sequence thereof.

Because properties of the hinge region determine the post-translational modification of proteases, the ratio of dimers to monomers can be effectively controlled by selecting proper hinge regions. In addition, when inclusion bodies are refolded, the formation of accurate dimers is hindered by the mismatching of cysteins in disulfide bonds. However, the method according to the present invention ensures the formation of accurate disulfide bonds, thereby leading to the formation of active dimers.

In addition, the present invention can produce immunoglobulin Fc regions on a larger scale than can conventional methods. For example, an immunoglobulin Fc region is produced at a yield of 15 mg/L according to the method of European Pat. No. EP0227110, in which a G1 Fc region is overexpressed and purified only from a cell lysate containing the water-soluble form thereof, and at a yield of 50 to 600 mg/L according to the method of Korean Pat. Appl'n No. 0092783, in which an immunoglobulin Fc region fused to an $E.$ $coli$ signal sequence is expressed in a water-soluble form, but not as an inclusion body. However, the present invention can produce an immunoglobulin Fc region at a yield of as high as 3 to 6 g/L by purifying an inclusion body of a recombinant immunoglobulin Fc region containing a hinge region. Thus, the method of the present invention ensures a highly useful system for producing immunoglobulin Fc regions on an industrial scale at much higher yield than to conventional methods.

In another aspect, the present invention relates to an immunoglobulin Fc region prepared according to the above method.

The immunoglobulin Fc region produced in prokaryotic cells such as $E.$ $coli$ according to the present method does not have specifically limited industrial applications. One exemplary application is use as a carrier for the formation of a conjugate with a certain drug. Construction of the conjugate comprising the immunoglobulin Fc region linked to a drug is not specifically limited. For example, the immunoglobulin Fc region and the drug may be linked together at various ratios, and the linkage may be mediated, for example, through a linker.

The drug includes polypeptides, compounds, extracts and nucleic acids. Preferred is a polypeptide drug (used to have a meaning identical to the word "protein"). Examples of the linker useful in the present invention include peptide and non-peptide linkers, with preference for a non-peptide linker and higher preference for a non-peptide polymer. A preferred example of the immunoglobulin heavy chain is Fc.

If the serum half-life needs to be enhanced, any physiologically active polypeptide may be used without specific limitation as a protein partner of the immunoglobulin Fc region prepared according to the present method to form a conjugate. Such physiologically active polypeptides include those used for treating or preventing human diseases, which include cytokines, interleukins, interleukin binding protein, enzymes, antibodies, growth factors, transcription regulatory factors, coagulation factors, vaccines, structural proteins, ligand proteins or receptors, cell surface antigens, receptor antagonists, and derivatives and analogues thereof.

In detail, non-limiting examples of the physiologically active polypeptide include human growth hormone, growth hormone releasing hormone, growth hormone releasing peptide, interferons and interferon receptors (e.g., interferon-α, -β and -γ, water-soluble type I interferon receptor, etc.), colony stimulating factors, interleukins (e.g., interleukin-1, -2, -3, -4, -5, -6, -7, -8, -9, -10, -11, -12, -13, -14, -15, -16, -17, -18, -19, -20, -21, -22, -23, -24, -25, -26, -27, -28, -29, -30, etc.) and interleukin receptors (e.g., IL-1 receptor, IL-4 receptor, etc.), enzymes (e.g., glucocerebrosidase, iduronate-2-sulfatase, alpha-galactosidase-A, agalsidase alpha and beta, alpha-L-iduronidase, butyrylcholinesterase, chitinase, glutamate decarboxylase, imiglucerase, lipase, uricase, platelet-activating factor acetylhydrolase, neutral endopeptidase, myeloperoxidase, etc.), interleukin and cytokine binding proteins (e.g., IL-18 bp, TNF-binding protein, etc.), macrophage activating factor, macrophage peptide, B cell factor, T cell factor, protein A, allergy inhibitor, cell necrosis glycoproteins, immunotoxin, lymphotoxin, tumor necrosis factor, tumor suppressors, metastasis growth factor, alpha-1 antitrypsin, albumin, alpha-lactalbumin, apolipoprotein-E, erythropoietin, highly glycosylated erythropoietin, angiopoietins, hemoglobin, thrombin, thrombin receptor activating peptide, thrombomodulin, factor VII, factor VIIa, factor VIII, factor IX, and factor XIII, plasminogen activating factor, fibrin-binding peptide, urokinase, streptokinase, hirudin, protein C, C-reactive protein, renin inhibitor, collagenase inhibitor, superoxide dismutase, leptin, platelet-derived growth factor, epithelial growth factor, epidermal growth factor, angiostatin, angiotensin, bone growth factor, bone stimulating protein, calcitonin, insulin, atriopeptin, cartilage inducing factor, elcatonin, connective tissue activating factor, tissue factor pathway inhibitor, follicle stimulating hormone, luteinizing hormone, luteinizing hormone releasing hormone, nerve growth factors (e.g., nerve growth factor, ciliary neurotrophic factor, axogenesis factor-1, brain-natriuretic peptide, glial derived neurotrophic factor, netrin, neurophil inhibitor factor, neurotrophic factor, neuturin, etc.), parathyroid hormone, relaxin, secretin, somatomedin, insulin-like growth factor, adrenocortical hormone, glucagon, cholecystokinin, pancreatic polypeptide, gastrin releasing peptide, corticotropin releasing factor, thyroid stimulating hormone, autotaxin, lactoferrin, myostatin, receptors (e.g., TNFR (P75), TNFR (P55), IL-1 receptor, VEGF receptor, B cell activating factor receptor, etc.), receptor antagonists (e.g., IL1-Ra etc.), cell surface antigens (e.g., CD 2, 3, 4, 5, 7, 11a, 11b, 18, 19, 20, 23, 25, 33, 38, 40, 45, 69, etc.), monoclonal antibodies, polyclonal antibodies, antibody fragments (e.g., scFv, Fab, Fab', F(ab')2 and Fd), and virus derived vaccine antigens. The physiologically active polypeptide useful in the present invention may be a native form, may be produced by genetic recombination using prokaryotic cells, such as E. coli, or eukaryotic cells, such as yeast cells, insect cells and animal cells, or may be a derivative having one or more amino acid mutations but showing biological activity identical to that of the native form.

In a preferred embodiment of the present invention, an immunoglobulin Fc region fragment produced using the HM11201 transformant was linked to human erythropoietin (EPO) using polyethylene glycol, thus providing an EPO-PEG-immunoglobulin Fc region protein conjugate. This protein conjugate was found to exhibit extended serum half-life compared not only to the native EPO but also to Aranesp (Amgen), known as a second generation EPO having improved serum half-life. Thus, the immunoglobulin Fc region devoid of the initial methionine residue, obtained from inclusion bodies using a hinge region in accordance with the present invention, can be used to enhance the serum half-life and physiological activity of the physiologically active polypeptide linked thereto, with no risk of immune response induction.

A better understanding of the present invention may be obtained through the following examples which are set forth to illustrate, but are not to be construed as the limit of the present invention.

EXAMPLE 1

Construction of Human Immunoglobulin IgG4 Fc Region Expression Vector, Expression and Purification of IgG4 Fc Region, and N-Terminal Sequence Analysis <1-1> Construction of IgG4 Fc Region Expression Vector To clone a heavy chain Fc region including the hinge region of human immunoglobulin IgG4, RT-PCR was carried out with RNA from human blood cells serving as a template, as follows. First, total RNA was isolated from about 6 ml of blood using a Qiamp RNA blood kit (Qiagen), and gene amplification was performed using the total RNA as a template with the aid of a One-Step RT-PCR kit (Qiagen). To amplify genes having different N-terminal sequences, pairs of primers represented by SEQ ID NOS. 1 and 2, 3 and 2, 4 and 2, and 5 and 2 were used. To facilitate a subsequent gene cloning procedure, an Nde I recognition site and the initiation codon ATG, necessary for protein expression, were introduced into 5' primers of SEQ ID NOS. 1, 3, 4 and 5, and a BamHI recognition site containing a stop codon into 3' primers of SEQ ID NO. 2. The amplified Fc region products were digested with Nde I and Hind III, and inserted into a pET22b (Novagen) treated with the same restriction enzyme, thus giving respective recombinant plasmids. These plasmids were designed to have parts of the total amino acid sequence Glu-Ser-Lys-Tyr-Gly-Pro-Pro-Cys-Pro-Ser-Cys-Pro (SEQ ID NO: 17) of the IgG4 hinge region, as follows.

The plasmid which contained a gene amplified with SEQ ID NOS. 1 and 2 was named pmSCPFc and anchored thereto a DNA sequence coding for an N-terminal amino acid sequence starting with Met-Ser-Cys-Pro (SEQ ID NO: 61), which was determined through base sequencing to have SEQ ID NO. 6, corresponding to the amino acid sequence of SEQ ID NO. 7. The plasmid which contained a gene amplified with SEQ ID NOS. 3 and 2 was named pmPSCFc and anchored thereto a DNA sequence coding for an N-terminal amino acid sequence starting with Met-Pro-Ser-Cys-Pro (SEQ ID NO: 62), which was determined through base sequencing to have SEQ ID NO. 8, corresponding to the amino acid sequence of SEQ ID NO. 9. A plasmid which contained a gene amplified with SEQ ID NOS. 4 and 2 was named pmCPSFc and anchored thereto a DNA sequence coding for an N-terminal amino acid sequence starting with Met-Cys-Pro-Ser-Cys-Pro (SEQ ID NO: 63), which was determined through base sequencing to have SEQ ID NO. 10, corresponding to the amino acid sequence of SEQ ID NO. 11. A plasmid which contained a gene amplified with SEQ ID NOS. 5 and 2 was named pmCPFc and anchored thereto a DNA sequence coding for an N-terminal amino acid sequence starting with Met-Cys-Pro, which was determined through base sequencing to have SEQ ID NO. 12 corresponding to SEQ ID NO. 13.

The expression vectors were transformed into E. coli BL21 (DE3) to prepare transformants respectively designated BL21/pmSCPFc (HM11200), BL21/pmPSCFc (HM11201), BL21/pmCPSFc (HM11204) and BL21/pmCPFc (HM11205). The transformants BL21/pmSCPFc (HM11200) and BL21/pmPSCFc (HM11201) were deposited at the Korean Culture Center of Microorganisms (KCCM) of 361-221, Yurim B/D, Hongje-1-dong, Seodaemun-gu, Seoul 120-091, Republic of Korea, on Jun. 20, 2005 with Accession Nos. KCCM-10659P and KCCM-10660P, respectively, and the transformants BL21/pmCPSFc (HM11204) and BL21/pmCPFc (HM11205) at KCCM on Jul. 28, 2005 with Accession Nos. KCCM-10665P and KCCM-10666P, respectively, under the Budapest Treaty on the International Recognition of the Deposit of Microorganisms For the Purposes of Patent Procedure.

<1-2> Expression and Purification of IgG4 Fc

The bacterial transformants prepared in Example <1-2> were inoculated in respective fermentors (Marubishi Company) and allowed to grow, followed by determining whether they expressed immunoglobulin Fc region fragments.

First, each transformant was grown in 100 ml of LB medium with agitation overnight, and inoculated in a fermentor for large-scale culture. The fermentor was maintained at 28° C. or 35° C. To prevent conversion from an aerobic to an anaerobic environment, the cultures were aerated with 20-vvm air and stirred at 500 rpm. To compensate for the insufficient nutrients for bacterial growth during fermentation, the cultures were supplemented with glucose and yeast extracts according to the fermentation states of bacteria. When the cultures reached an $OD_{600}$ value of 80, an inducer, IPTG, was added to the cultures to induce protein expression. The cultures were further cultured for 40 to 45 hrs to increase the OD value at 600 nm to 100 to 120.

The expression of immunoglobulin Fc, the formation of inclusion bodies, and the dimer formation of the expressed Ig Fc in the E. coli transformants were examined as follows. To investigate the overall intracellular expression of the immunoglobulin Fc regions, parts of the fermented solutions were mixed with equal volumes of 2× protein sample buffer and electrophoresed on a 15% SDS-PAGE gel (Criterion Gel, Bio-Rad). As a result, immunoglobulin Fc was observed to be overexpressed in all of the transformants produced. Then, cells were disrupted using an ultrasonicator (Misonix Company). The cell lysate thus obtained was centrifuged to separate water-soluble substances from water-insoluble substances. Most of the overexpressed substances were found to exist as inclusion bodies, as measured by electrophoresis on 15% SDS-PAGE. The inclusion bodies were subjected to the following refolding process in order to examine to what degree Fc was refolded and whether and to what degree dimeric Fc regions were formed. 10 g of the fermented solution was subjected to ultrasonication in 100 mL of a lysis buffer (10 mM Tris, pH 9.0, 1 mM EDTA, 0.5% Triton X-100, 0.2M NaCl) to disrupt the cells. Centrifugation at 10,000 rpm for 20 min divided the cell lysate into a water-soluble fraction and a water-insoluble fraction as an inclusion body. 2 g of this inclusion body was dissolved in a mixture of 20 mL of 1M Tris (pH 9.0) and 20 mL of a solubilization buffer (6M Guanidine, 50 mM Tris) and allowed to react while being gently agitated at 4° C. for 30 min. Following completion of the reaction, the inclusion body solution was mixed overnight with 10 volumes of a refolding buffer (2 M urea, 50 mM Tris, 0.25 M Arginine, 3 mM cysteine, pH 9.0) with gentle agitation. To this mixture was added a protein sample buffer free from any reducing agent, such as DTT or beta-mercaptoethanol, followed by electrophoresis on 15% SDS-PAGE (Criterion Gel, Bio-Rad). The protein bands were visualized with a dye such as Coomassie Brilliant. FIG. 1 is a photograph taken of a gel on which proteins refolded from the inclusion bodies expressed by the reformant HM11201 at 32° C. (lane 1) and 28° C. (lane 2), by HM11200 at 28° C. (lane 3) and 32° C. (lane 4), by HM11204 at 28° C. (lane 5) and 32° C. (lane 6), and by HM11205 at 32° C. (lane 7) and 28° C. (lane 8) were run in the presence of an electric field, along with an Fc protein, as a control, purified from E. coli according to a conventional method (lane C). As seen in FIG. 1, a significant portion of the total proteins is attributed to the Fc protein, much of which exists in a dimeric form after being refolded. However, the Fc proteins differ in the ratio of dimers to monomers from one transformant to another, that is, according to the N-terminal amino acid sequence expressed by the transformant. For example, a significant portion of the Fc proteins of HM11201, which starts with Met-Pro-Ser-Cys-Pro-CH2—CH3 (SEQ ID NO: 62), exists in a dimeric form. Almost all of the Fc proteins of HM11205, which start with Met-Cys-Pro-CH2-CH3, exist as monomers, but neither exist in dimeric forms. This is believed to be attributed to the fact that the processing specificity of aminopeptidase in E. coli host cells varies depending on the Fc N-terminal sequence.

<1-3> N-Terminal Sequence Analysis

The dimeric Fc region fragments refolded from the inclusion bodies are different in amino acid sequence from the wild type because of the presence of the initial methionine residue. In order to determine whether the methionine residue is processed by E. coli proteases, N-terminal amino acid sequences of the proteins were analyzed by the Basic Science Research Institute, Seoul, Korea. The samples used in the N-terminal amino acid sequence analysis were prepared as follows.

First, a PVDF membrane (Bio-Rad) was immersed in methanol for about 2-3 sec to activate it, and was sufficiently wet with a blocking buffer (170 mM glycine, 25 mM Tris-HCl (pH 8.0), 20% methanol). The protein samples separated on a non-reduced SDS-PAGE gel, prepared in Example <1-2>, were blotted onto a PVDF membrane for about one hour using a blotting kit (Hoefer Semi-Dry Transfer unit, Amersham). Proteins transferred onto the PVDF membrane were stained with a protein dye, Coomassie Blue R-250 (Amnesco), for a moment (3-4 sec), and washed with a destaining solution (water: acetic acid: methanol=5:1:4). Then, membrane fragments containing proteins were cut out with scissors and subjected to N-terminal sequence analysis.

As a result, the IgG4 Fc proteins including a hinge region were found to have an N-terminal sequence of Glu-Ser-Lys-Tyr-Gly-Pro-Pro-Cys Pro-Ser-Cys-Pro-CH2—CH3 (SEQ ID NO: 17). Amino acid sequences and N-terminal sequences of the proteins expressed in the transformants are given in the following Table 1.

TABLE 1

| Trans- | | Results of sequence analysis | |
|---|---|---|---|
| formants | N-terminal sequences | dimer | Monomer |
| HM11200 | Met-Ser-Cys-Pro-CH2- (SEQ ID NO: 61) | Ser-Cys-Pro-CH2 (SEQ ID NO: 18) | Pro-CH2 |
| HM11201 | Met-Pro-Ser-Cys-Pro-CH2- (SEQ ID NO: 62) | Pro-Ser-Cys-Pro-CH2 (SEQ ID NO: 19) | Pro-Ser-Cys-Pro-CH2 (SEQ ID NO: 19) |
| HM11204 | Met-Cys-Pro-Ser-Cys-Pro-CH2 (SEQ ID NO: 63) | Pro-Ser-Cys-Pro-CH2 (SEQ ID NO: 19) | mixed |
| HM11205 | Met-Cys-Pro-CH2-CH3 | — | Pro-CH2 |

Data from the amino acid sequencing analysis revealed that the Fc fragments refolded from the inclusion bodies produced by the E. coli transformants of the present invention were processed to have an accurate N-terminal sequence devoid of the initial methionine residue. The protein product which remains in a monomeric form even after refolding is deprived of cystein residues, and thus it cannot form dimers. In addition, as apparent from FIG. 1, the portion of monomer in the refolded Fc fragments differs from one transformant to another, and no dimers exist in HM11205. These results indicate that the amino acid sequence of the N terminal site has a great influence on the processing of the N terminus, so that a protein having a desired N-terminal sequence can be obtained by modulating the N-terminal sequence. Proteins, even if they have the same amino acid sequence, can be differently processed depending on the culture conditions of E. coli host cells, especially culture temperature, as revealed through the following tests. HM11200, when grown at low temperatures (28° C.~32° C.), expressed the Fc fusion protein in a solubilized form in the same amount as in the inclusion body form. The solubilized form of the Fc fusion protein existed as a monomer devoid of the N-terminal amino acid sequence Met-Ser-Cys. Thus, the present inventors recognized that a controlled proportion of monomeric and dimeric immunoglobulin Fc fragments can be obtained by modulating the N-terminal amino acid sequence of the fusion Fc protein and the culture condition of host cells.

To quantitatively determine the expression of immunoglobulin Fc regions in the *E. coli* transformants, immunoglobulin Fc regions of the refolding solution were purified using a protein-A affinity column known to have strong affinity to immunoglobulins, as follows.

Inclusion bodies collected by centrifugation were refolded, and then purified through column chromatography. After 5 ml of a protein-A affinity column (Pharmacia) was equilibrated with PBS, the cell lysates were loaded onto the column at a flow rate of 5 ml/min. Unbound proteins were washed out with PBS, and bound proteins were eluted with 100 mM citrate (pH 3.0). The collected fractions were desalted using a HiPrep 26/10 desalting column (Pharmacia) with 10 mM Tris buffer (pH 8.0). Then, secondary anion exchange column chromatography was carried out using 50 ml of a Q HP 26/10 column (Pharmacia). The primary purified recombinant immunoglobulin Fc regions were loaded onto the Q-Sepharose HP 26/10 column (pharmacia), and the column was eluted with a linear gradient (0-0.2 M NaCl) in 10 mM Tris buffer (pH 8.0), thus providing highly pure fractions. After being partially purified using the protein-A affinity column, expression levels of the recombinant Ig Fc regions were determined, and the results are given in Table 2, below.

TABLE 2

| Plasmids | Transformants | Expression Yields After Protein-A Purification |
|---|---|---|
| pmSCPFc | HM11200 | 5-6 g/L |
| pmPSCFc | HM11201 | 4-5 g/L |
| pmCPSFc | HM11204 | 4-5 g/L |
| pmCPFc | HM11205 | 3-4 g/L |

EXAMPLE 2

Construction of Human Immunoglobulin IgG1 Fc Region Expression Vector, Expression and Purification of IgG1 Fc Region, and N-Terminal Sequence Analysis <2-1> Construction of IgG1 Fc Region Expression Vector To clone a heavy chain Fc region including the hinge region of human immunoglobulin IgG1, RT-PCR was carried out in the same manner as in Example <1-1>. To amplify genes having different N-terminal sequences, the following primers were used.

TABLE 3

| | SEQ ID NO: | 5' Primer Sequence | SEQ ID NO: |
|---|---|---|---|
| MEPK | 64 | 5'GGA ATT CCA TAT GGA GCC CAA ATC TTG TGA CAA AAC TCA C 3' | 72 |
| MSCD | 65 | 5'GGA ATT CCA TAT GTC TTG TGA CAA AAC TCA CAC ATG CCC 3' | 73 |
| MDKT | 66 | 5'GGA ATT CCA TAT GGA CAA AAC TCA CAC ATG CCC ACC GTG C 3' | 74 |
| MCPA | 67 | 5'GGG ATT TCC ATA TGT GCC CAG CAC CTG AAC TCC TGG GG | 75 |
| MPKS | 68 | 5'GGG AAT TCC ATA TGC CCA AAT CTT GTG ACA AAA CTC AC | 76 |
| MCPP | 69 | 5'GGG AAT TCC ATA TGT GCC CAC CGT GCC CAG CAC CTG AAC TCC | 77 |
| MPPC | 70 | 5'GGA ATT CCA TAT GCC ACC GTG CCC AGC ACC TGA ACT CCT G 3' | 78 |

TABLE 3-continued

| | SEQ ID NO: | 5' Primer Sequence | SEQ ID NO: |
|---|---|---|---|
| MPCP | 71 | 5'GGA ATT CCA TAT GCC GTG CCC AGC ACC TGA ACT CCT GGG G 3' | 79 |

As for 3' primer, it had the sequence of 5'-CGC GGA TCC TCA TTT ACC CGG AGA CAG GGA GAG GCT CTT C-3' (SEQ ID NO: 80) and was used for the amplification of all of the genes having different N-terminal sequences. To facilitate a subsequent gene cloning procedure, an Nde I recognition site was introduced into each of the 5' primers, and a BamHI recognition site into the 3' primer. The Fc region products amplified with pairs of the primers were inserted into a vector, thus giving respective recombinant plasmids designed to have parts of the total amino acid sequence Glu-Pro-Lys-Ser-Cys-Asp-Lys-Thr-His-Thr-Cys-Pro-Pro-Cys-Pro (SEQ ID NO: 14) of the IgG1 hinge region as follows. The plasmid which contained a gene amplified with the MEPK (SEQ ID NO: 64) primer was named pMEPKFc1, and anchored thereto a DNA sequence coding for the CH2 and CH3 of IgG1, starting with Met-Glu-Pro-Lys (SEQ ID NO: 64), which was analyzed through base sequencing to have SEQ ID NO. 22 corresponding to the amino acid sequence of SEQ ID NO. 23. The plasmid, which contained a gene amplified with the MSCD (SEQ ID NO: 65) primer, was named pMSCKFc1 and anchored thereto a DNA sequence coding for the CH2 and CH3 of IgG1, starting with Met-Ser-Cys-Asp (SEQ ID NO: 65), which was analyzed through base sequencing to have SEQ ID NO. 24, corresponding to the amino acid sequence of SEQ ID NO. 25. A plasmid which contained a gene amplified with the MDKT (SEQ ID NO: 66) primer was named pMDKTFc1 and anchored thereto a DNA sequence coding for the CH2 and CH3 of IgG1, starting with Met-Asp-Lys-Thr (SEQ ID NO: 66), which was analyzed through base sequencing to have SEQ ID NO. 26 corresponding to the amino acid sequence of SEQ ID NO. 27. A plasmid which contained a gene amplified with the MCPA (SEQ ID NO: 67) primer was named pMCPAFc1 and anchored thereto a DNA sequence coding for the CH2 and CH3 of IgG1, starting with Met-Cys-Pro, which was analyzed through base sequencing to have SEQ ID NO. 28, which corresponds to SEQ ID NO. 29. A plasmid which contained a gene amplified with the MPKS (SEQ ID NO: 68) primer was named pMPKSFc1, and anchored thereto a DNA sequence coding for the CH2 and CH3 of IgG1, starting with Met-Pro-Lys-Ser (SEQ ID NO: 68), which was analyzed through base sequencing to have SEQ ID NO. 30, which corresponds to SEQ ID NO. 31. A plasmid which contained a gene amplified with the MCPP (SEQ ID NO: 69) primer was named pMCPPFc1, and anchored thereto a DNA sequence coding for the CH2 and CH3 of IgG1, starting with Met-Cys-Pro-Pro (SEQ ID NO: 69), which was analyzed through base sequencing to have SEQ ID NO. 32, which corresponds to SEQ ID NO. 33. A plasmid which contained a gene amplified with the MPPC (SEQ ID NO: 70) primer was named pMPPCFc, and anchored thereto a DNA sequence coding for the CH2 and CH3 of IgG1, starting with Met-Pro-Pro-Cys (SEQ ID NO: 70), which was analyzed through base sequencing to have SEQ ID NO. 34, which corresponds to SEQ ID NO. 35. A plasmid which contained a gene amplified with the MPCP (SEQ ID NO: 71) primer was named pMPCPFc, and anchored thereto a DNA sequence coding for the CH2 and CH3 of IgG1, starting with Met-Pro-Cys-Pro (SEQ ID NO: 71), which was analyzed through base sequencing to have SEQ ID NO. 36, corresponding to SEQ ID NO. 37. The expression vectors were transformed into *E. coli* BL21 (DE3) to prepare transformants respectively designated as BL21/pMEPKFc1(HM11206), BL21/pMSCDFc1(HM11207), BL21/pMDKTFc1(HM11208), BL21/pMCPAFc1 (HM11209) BL21/pMPKSFc1(HM11210), BL21/pMCP-PFc1(HM11211), BL21/pMPPCFc1(HM11212) and BL21/pMPCPFc1(HM11213).

<2-2> Expression and Purification of IgG1 Fc

As in the case of IgG4, bacterial transformants prepared in Example <2-1> were inoculated in respective fermentors (Marubishi Company) and allowed to grow, followed by determining whether they expressed immunoglobulin Fc region fragments.

First, each transformant was grown in 100 ml of LB medium with agitation overnight and inoculated in the fermentor for large-scale culture. The fermentor was maintained at 28° C. or 35° C. To prevent conversion from an aerobic to an anaerobic environment, the cultures were aerated with 20-vvm air and stirred at 500 rpm. To compensate for the insufficient nutrients for bacterial growth during fermentation, the cultures were supplemented with glucose and yeast extracts according to the fermentation states of bacteria. When the cultures reached an $OD_{600}$ value of 80, an inducer, IPTG, was added to the cultures to induce protein expression. The cultures were further cultured for 40 to 45 hrs to increase the OD value at 600 nm to 100 to 120.

The expression of immunoglobulin Fc, the formation of inclusion bodies, and the dimer formation of the expressed Ig Fc in the *E. coli* transformants were examined as follows. To investigate overall intracellular expression of the immunoglobulin Fc regions, the fermented solutions were aliquoted before and after the induction.

Figure 7:
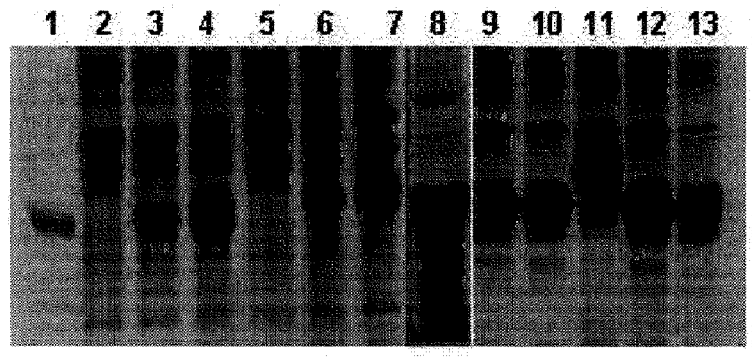
FIG. 7 is a photograph of a 15% SDS-PAGE gel on which after being mixed with equal volumes of a 2× protein sample buffer, parts of the fermented solutions obtained by growing microbial transformants of Example 2 in fermentors under an expression condition are run.

Parts of the fermented solutions were mixed with equal volumes of 2× protein sample buffer and electrophoresed on a 15% SDS-PAGE gel (Criterion Gel, Bio-Rad) under the following reducing conditions. The electrophoresis results are given in FIG. 7. A control of IgG4 Fc was run in lane 1, while the expression levels of the HM11208 transformant according to time are shown in lanes 2 to 4 and the expression levels of the HM11206 transformant according to time in lanes 5 to 7. Expression levels in HM11207, HM11212, HM11209, HM11210, HM11213 and HM11211 transformants are shown in lanes 8 to 13, respectively. As seen in FIG. 7, a single 30 kda-band (FC region), which was not observed before the IPTG induction, very clearly appeared in all of the samples subjected to IPTG induction, indicating that the recombinant IgG1 Fc regions were expressed by contrast with the G4Fc control. Also, the Fc regions were overexpressed, amounting to at least about 30% of the total amount of proteins expressed.

To quantitatively determine the expression of immunoglobulin Fc regions in the *E. coli* transformants, immunoglobulin Fc regions of the refolding solution were purified using a protein-A affinity column known to have strong affinity to immunoglobulin in the same manner as that used for IgG4 Fc.

Of the transformants, the pMSCDFc plasmid transformant was measured to have the highest expression rate, amounting to as much as 340 mg per 10 g of inclusion body, while the pMDKTFc, pMEPKFc, pMPPCFc and pMPCPFc transformants showed expression rates of 133.3 mg, 159 mg, 110 mg and 120 mg, respectively.

Contents of dimeric IgG1 Fc in the expressed products were measured in the same manner as that used for the content of dimeric IgF4 Fc. Cells of the fermentation solutions were disrupted using an ultrasonicator (Misonix Company). The cell lysate thus obtained was centrifuged to separate water-soluble substances from water-insoluble substances. Most of the overexpressed substances were found to exist as inclusion bodies as measured by electrophoresis on 15% SDS-PAGE. The inclusion bodies were refolded in order to examine to what degree Fc was refolded and whether and to what degree dimeric Fc regions were formed. The refolded Fc proteins were purified using a protein-A affinity column and mixed with a protein sample buffer free of a reducing agent, such as DIT or beta-mercaptoethanol, followed by electrophoresis on 15% SDS-PAGE (Criterion Gel, Bio-Rad). The protein bands were visualized with a dye such as Coomassie Brilliant.

Figure 8:
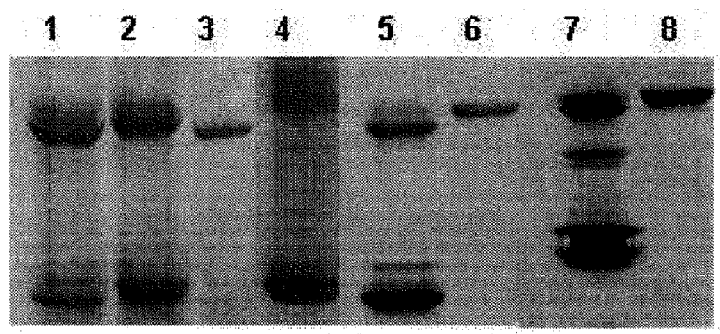
FIG. 8 is a photograph of an SDS-PAGE gel on which the proteins refolded from the inclusion bodies expressed by the transformants of Example 2 are separated and visualized as bands.

FIG. 8 is a photograph taken of a gel on which protein-A column isolates of the proteins refolded from the inclusion bodies expressed by the reformant HM11208 (lane 1), by the reformant HM11206 (lane 2), by the reformant HM11207 (lane 4), by the reformant HM11212 (lane 5) and by the reformant HM11213 (lane 7) were run in the presence of an electric field under a non-reducing condition, along with an IgG4 Fc protein used as a control (lanes 3, 6, and 8). As shown in FIG. 8, all of the IgG1 Fc fragments used in the test were found to form dimers, although the amount thereof differed to some degree.

<2-3> N-Terminal Sequence Analysis

As recognized in the case of IgG4 Fc, the N-terminal amino acid sequence determined the post-translational processing as to whether the initial methionine residue remained or whether the initial methionine residue was accurately processed, or along with other amino acid residues to give amino acid sequences different from the desired one. In order to examine whether the methionine residue was processed by *E. coli* proteases, different N-terminal amino acid sequences of the IgG1 Fc regions were analyzed by the Basic Science Research Institute, Seoul, Korea. The analysis results are summarized in Table 4, below.

TABLE 4

| Transformants | N-Terminal Sequencing Results (Dimers) |
|---|---|
| HM11208 | Met |
| HM11206 | Met |
| HM11207 | Ser |
| HM11212 | Pro |
| HM11213 | Pro |

As seen in Table 4, the initial methionine residue remains unprocessed in the transformants of HM11208 and HM11206, in which IgG1 Fc regions were overexpressed in dimeric forms while the fermented products of HM11207, HM11212 and HM11213 have no initial methionine residues as a result of the accurate post-translational processing.

Taken together, data obtained through the above-mentioned experiments indicate that when an IgG1 Fc region is expressed in *E. coli*, the N-terminal sequence thereof determines the expression, expression level, dimer proportion and N-terminal processing thereof, and that Fc regions devoid of initial methionine residues can be produced on a mass scale by taking advantage of the N-terminal sequence. The IgG1 Fc regions obtained according to the present invention can be used to enhance the serum half-life and physiological activity of the physiologically active polypeptide linked thereto without immune response induction due to the addition of exogenous amino acid residues.

EXAMPLE 3

Construction of Human Immunoglobulin IgG2 Fc Region Expression Vector

<3-1> Construction of IgG2 Fc Region Expression Vector

To clone a heavy chain Fc region including the hinge region of IgG2, RT-PCR was carried out in the same manner as that used for IgG4 Fc region. To amplify genes having different N-terminal sequences, the following primers were used.

TABLE 5

|  | 5' Primer Sequences | SEQ ID NO: |
|---|---|---|
| G2MPPCSS | 5' GGG AAT TCC ATA TGC CAC CGT GCC CAG CAC CAC CTG TGG CAG G 3' | 81 |
| G2MPCPSS | 5' GGG AAT TCC ATA TGC CGT GCC CAG CAC CAC CTG TGG CAG GAC 3' | 82 |
| G2MCPSS | 5' GGG AAT TCC ATA TGT GCC CAG CAC CAC CTG TGG CAG GAC 3' | 83 |
| G2MCCVSS | 5' GGG AAT TCC ATA TGT GTT GTG TCG AGT GCC CAC CGT GCC CAG C 3' | 84 |
| G2MCVESS | 5' GGG AAT TCC ATA TGT GTG TCG AGT GCC CAC CGT GCC CAG CAC C 3' | 85 |

The 3' primer had the sequence of 5'-CGC GGA TCC TCA TTT ACC CGG AGA CAG GGA GAG GCT CTT C-3' (SEQ ID NO: 80) and was applied for the amplification of all of the genes having different N-terminal sequences. To facilitate a subsequent gene cloning procedure, an Nde I recognition site was introduced into each of the 5' primers, and a BamHI recognition site into the 3' primer. The Fc region products amplified with pairs of the primers were inserted into a vector, thus giving respective recombinant plasmids designed to have parts of the total amino acid sequence Glu-Arg-Lys-Cys-Cys-Val-Glu-Cys-Pro-Pro-Cys-Pro (SEQ ID NO: 15) of the IgG1 hinge region, as follows. The plasmid which contained a gene amplified with the G2MPPCSS primer was named pmPPCG2Fc and anchored thereto a DNA sequence coding for the CH2 and CH3 of IgG2, starting with Met-Pro-Pro-Cys (SEQ ID NO: 70), which was analyzed through base sequencing to have SEQ ID NO. 38, corresponding to the amino acid sequence of SEQ ID NO. 39. The plasmid which contained a gene amplified with the G2MPCPSS primer was named pmPCPG2Fc and anchored thereto a DNA sequence coding for the CH2 and CH3 of IgG2, starting with Met-Pro-Cys-Pro (SEQ ID NO: 71), which was analyzed through base sequencing to have SEQ ID NO. 40, corresponding to the amino acid sequence of SEQ ID NO. 41. A plasmid which contained a gene amplified with the G2MCPSS primer was named pmCPG2Fc and anchored thereto a DNA sequence coding for the CH2 and CH3 of IgG2, starting with Met-Cys-Pro, which was analyzed through base sequencing to have SEQ ID NO. 42, corresponding to the amino acid sequence of SEQ ID NO. 43. A plasmid which contained a gene amplified with the G2MCCVSS primer was named pmCCVG2Fc, and anchored thereto a DNA sequence coding for the CH2 and CH3 of IgG2, starting with Met-Cys-Cys-Val-Glu-Cys-Pro-Pro-Cys-Pro (SEQ ID NO: 86), which was analyzed through base sequencing to have SEQ ID NO. 44, which corresponded to SEQ ID NO. 45. A plasmid which contained a gene amplified with the G2MCVESS primer was named pmCVEG2Fc and anchored thereto a DNA sequence coding for the CH2 and CH3 of IgG2, starting with Met-Cys-Val-Glu-Cys-Pro-Pro-Cys-Pro (SEQ ID NO: 87), which was analyzed through base sequencing to have SEQ ID NO. 46, which corresponds to SEQ ID NO. 47. The expression vectors were transformed into *E. coli* BL21 (DE3) to prepare transformants respectively designated BL21/pmPPCPG2Fc (HM11206), BL21/pmPCPG2Fc (HM11207), BL21/pmCPG2Fc (HM11216), BL21/pmCCVG2Fc (HM11217) and BL21/pmCVEG2Fc (HM11218).

<3-2> Expression, Purification and N-terminal Sequence Analysis of IgG2 Fc

Figure 9:
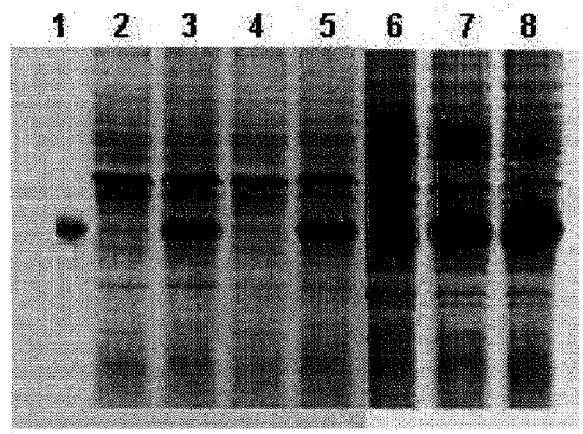
FIG. 9 is a photograph of a 15% SDS-PAGE gel on which after being mixed with equal volumes of a 2× protein sample buffer, parts of the fermented solutions obtained by growing microbial transformants of Example 3 in fermentors under an expression condition are run.

As in the case of IgG4, the bacterial transformants prepared in Example <3-1> were inoculated in respective fermentors (Marubishi Company) and allowed to grow, followed by determining whether they expressed immunoglobulin Fc region fragments. The culture conditions were not significantly different from those set forth for IgG4 Fc. The IgG2 Fc region fragments were found to be overexpressed under various conditions, including temperature, medium composition, inducer concentration, etc. as measured by SDS-PAGE in a reducing condition. FIG. 9 shows the result of a 15% SDS-PAGE of the fermentation solutions mixed with equal volumes of 2× protein sample buffer. An IgG4 Fc fragment was used as a control in lane 1 while the fragments expressed by the HM11214, HM11215, HM11216, HM11217 and HM11218 were run in lanes 2 to 6, respectively. As seen in FIG. 9, all of the five transformants used in the experiment overexpressed the Fc fragments.

Figure 10:
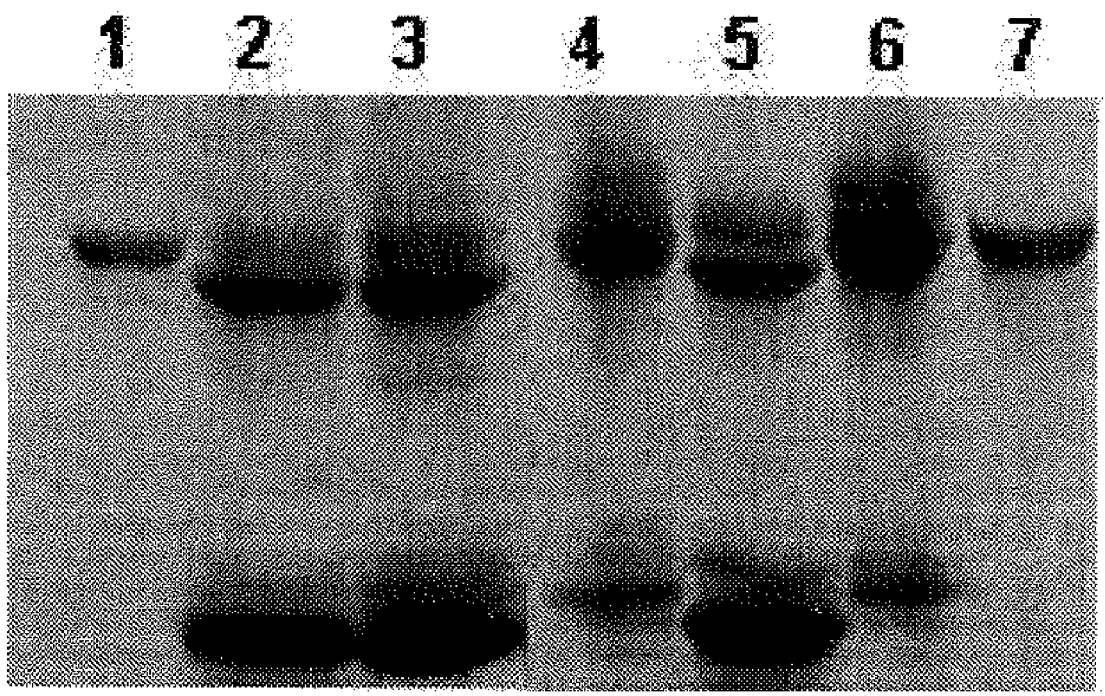
FIG. 10 is a photograph of a 15% SDS-PAGE gel on which after being mixed with a protein sample buffer free of a reducing agent such as DTT or beta-mercaptoethanol, the respective products expressed and purified in Example 3 are run.

The content of dimeric IgG4 Fc in the expressed products was measured in the same manner as described above. Cells of the fermentation solutions were disrupted and the water-insoluble substances of the cell lysate were refolded, after which only Fc region fragments were purified using a protein-A affinity column. The purified expression products were mixed with a protein sample buffer free of a reducing agent, such as DTT or beta-mercaptoethanol, and separated on 15% SDS-PAGE (Criterion Gel, Bio-Rad). The protein bands were visualized with a dye such as Coomassie Brilliant. FIG. 10 shows the result of electrophoresis. An IgG4 Fc fragment was used as a control in lanes 1 and 7 while dimers of the fragment from the HM11214, HM11215, HM11216, HM11217, and HM11218 were observed in lanes 2 to 6. As is understood from data of FIG. 10, the expression products of the transformants, although different from one another with respect to N-terminal sequence or expression condition, can all form dimers.

In order to examine whether the methionine residue is processed by *E. coli* proteases, different N-terminal amino acid sequences of the dimeric IgG4 Fc regions were analyzed by the Basic Science Research Institute in Seoul, Korea. The initial methionine residue was removed from the products from the HM11214 and HM11215 transformants, both of which have a proline residue at position 2.

As apparent from these experiments, IgG2 Fc regions can be expressed on a large scale in *E. coli*. In addition, data obtained in the above-mentioned experiments indicate that the N-terminal sequence of an IgG1 Fc region determines the expression, expression level, dimer proportion and N-terminal processing thereof, and that Fc regions devoid of initial methionine residues can be produced on a mass scale by taking advantage of the N-terminal sequence. The IgG1 Fc regions obtained according to the present invention can be used to enhance the serum half-life and physiological activity of the physiologically active polypeptide linked thereto without immune response induction due to the addition of exogenous amino acid residues.

EXAMPLE 4

C1q Binding Assay-Using ELISA

To determine whether the derivatives prepared in Example <1-2> and proteins corresponding to the Fc regions of immunoglobulins, expressed in the *E. coli* transformants and purified, bind to human C1q, an enzyme linked immunosorbent assay (ELISA) was carried out as follows. As test groups, immunoglobulin Fc regions produced by the HM11200 and HM11201 transformants prepared in the above Examples were used. As standards, a glycosylated immunoglobulin (IVIGG-globulin S, Green Cross PBM) was used. The test and standard samples were prepared in 10 mm carbonate buffer (pH 9.6) at a concentration of 1 µg/ml. The samples were aliquotted into a 96-well plate (Nunc) in an amount of 200 ng per well, and the plate was coated overnight at 4° C. Then, each well was washed with PBS-T (137 mM NaCl, 2 mM KCl, 10 mM $Na_2HPO_4$, 2 mM $KH_2PO_4$, 0.05% Tween 20) three times, blocked with 250 µl of a blocking buffer (1% bovine serum albumin in PBS-T) at room temperature for 1 hr, and washed again with the same PBS-T three times. The standard and test samples were diluted in PBS-T to a predetermined concentration and added to antibody-coated wells, and the plate was incubated at room temperature for 1 hr and washed with PBS-T three times. Thereafter, 2 µg/ml C1q (R&D Systems) was added to the plate and reacted at room temperature for 2 hrs, and the plate was washed with PBS-T six times. 200 µl of a 1:1000 dilution of a human anti-human C1q antibody-peroxidase conjugate (Biogenesis, USA) in the blocking buffer was added to each well and reacted at room temperature for 1 hr. After each well was washed with PBS-T three times, equal volumes of color reagents A and B (Color A: stabilized peroxide and Color B: stabilized chromogen; DY 999, R&D Systems) were mixed, and 200 µl of the mixture was added to each well, followed by incubation for 30 min. Then, 50 µl of a reaction termination solution, 2 M sulphuric acid, was added to each well. The plate was read using a microplate reader (Molecular Device). The absorbance of standard and test samples was measured at 450 nm, and the results are given in FIG. 2.

Figure 2:
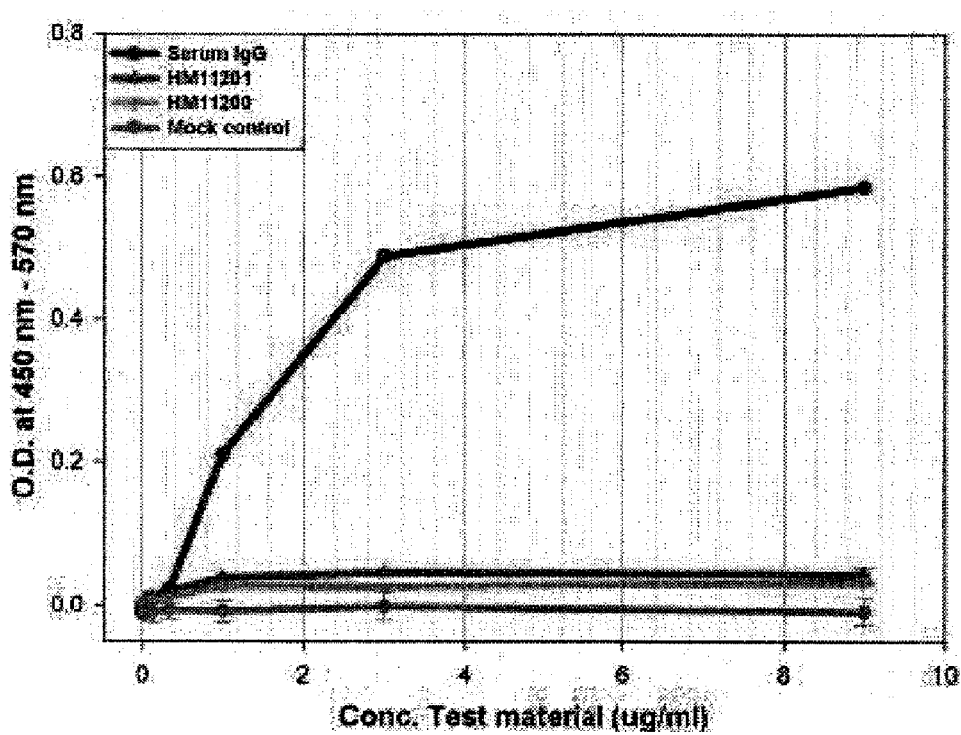
FIG. 2 shows the results of ELISA for the C1q binding capacity of human immunoglobulin IgG4 Fc region.

As shown in FIG. 2, the immunoglobulin Fc region proteins produced in *E. coli* according to the present invention exhibited markedly reduced binding affinity to C1q. These results indicate that the immunoglobulin Fc region proteins of the present invention rarely have the risk of inducing immune responses such as cytotoxicity and inflammation in the body when used as a carrier for physiologically active polypeptides in a conjugate form.

EXAMPLE 5

Assay for Binding to FcγRI, FcγRIII and $FcRn\alpha\beta_2$ Using ELISA

Immunoglobulin Fc is known to bind to the hematocyte receptors to FcγRI and FcγRIII to mediate effector functions such as antibody-dependent cytotoxicity. To determine whether the immunoglobulin Fc produced in *E. coli* mediates such effector functions, each of the receptors was obtained and assayed for binding ability through ELISA. Also, the immunoglobulin Fc was assayed for binding to the receptor FcRn, which is known to have influence on the in vivo metabolism of immunoglobulin, in the same manner.

<5-1> Construction of Human FcγRI, FcγRIII and $FcRn\alpha\beta_2$ Expression Strains Total RNA was isolated from human peripheral blood mononuclear cells using a kit (Qiagen, Cat. No. ???), and was used to fish for genes encoding extracellular ligand binding domains of human FcγRI, FcγRIII and $FcRn\alpha\beta_2$ through RT-PCR and PCT. The genes were fused to a GST (Glutathione S-transferase) gene and cloned in respective mammal cell expression vectors anchoring thereto a dehydrofolate reductase gene. The recombinant PHM000 plasma thus prepared was transfected into CHO cells. In this regard, CHO cells were inoculated at a count of $1\times10^6$ cells per 6-cm culture dish, incubated at 37° C. or 24 hours in a 5% $CO_2$ incubator, and washed twice with Opti-MEM (Gibco., Cat. no. 31985-070). 1 ml of the Opti-MEM containing 10 µg of PHM000 was mixed with 1 ml of Lipofectamine™ Reagent (Invitrogen, Cat. no. 18324-020). After being allowed to stand for 20 min, the resulting mixture was added to the prepared CHO cells. These cells were incubated at 37° C. for 18 hours in a 5% $CO_2$ incubator and refreshed with DMEM/F12, supplemented with 10% fetal bovine serum and 1% penicillin-streptomycin, before incubation for an additional 48 hours. In order to select transformed strains, the cells were treated with 0.5% trypsin (Gibco., Cat. no. 15400-054) in the selection medium α-MEM (Welgene, Cat. no. $LM008-O_2$) which included 10% dialyzed fetal bovine serum, 1% penicillin-streptomycin, and 800 ug/ml of geneticin (Mediatech, Cat. No. 61-234RG), followed by centrifugation. The cells thus transformed were transferred to a T25 culture dish (Nunc) and cultured at 37° C. in a 5% $CO_2$ incubator to 90% or higher confluency. In order to determine the expression levels of FcγRI, FcγRIII and $FcRn\alpha\beta_2$, the selected strains were incubated at 37° C. in a 5% $CO_2$ incubator with increasing concentrations of MTX (Sigma, Cat. No. M-8407) from 20 nM by an increment of 20 nM every two weeks.

<5-2> Production and Purification of Human FcγRI, FcγRIII and $FcRn\alpha\beta_2$ FcγRI, FcγRIII and $FcRn\alpha\beta_2$ were purified as follows. The selected cell strains were inoculated in Cell Factory (Nunc, Cat. no. 170009) at a count of $3.5\times10^8$ cells per factory and grown at 37° C. for 48 hours in a 5% $CO_2$ incubator, and then washed twice with 1 liter of PBS per factory. The cells were supplemented with 1 liter of the production medium CHO-A-SFM containing 0.3 mM sodium butyrate (Sigma, Cat. no. B-5887) and cultured at 33° C. in a 5% $CO_2$ incubator, during which the expression supernatant was recovered every other day 7 times in total. The collected supernatant was centrifuged, filtered through a 0.22 µm filtering system (Corning), concentrated using a concentration system (PALL, Cat. no. PN OS010C70), and loaded on a chelating sepharose FF resin (Amersharm pharmacia, Cat. no. 17-0575-02) charged with 0.1M nickel sulfide (Sigma, Cat. no. N4887), so that the GST of FcγRI, FcγRIII, and $FcRn\alpha\beta_2$ were bound to the nickel. Bound FcγRI, FcγRIII, and $FcRn\alpha\beta_2$ were separated and purified from the column using 50 mM NaPi (pH 8.0), 300 mM NaCl, and 250 mM imidazole.

<5-3> Assay for binding to FcγRI

Figure 3:
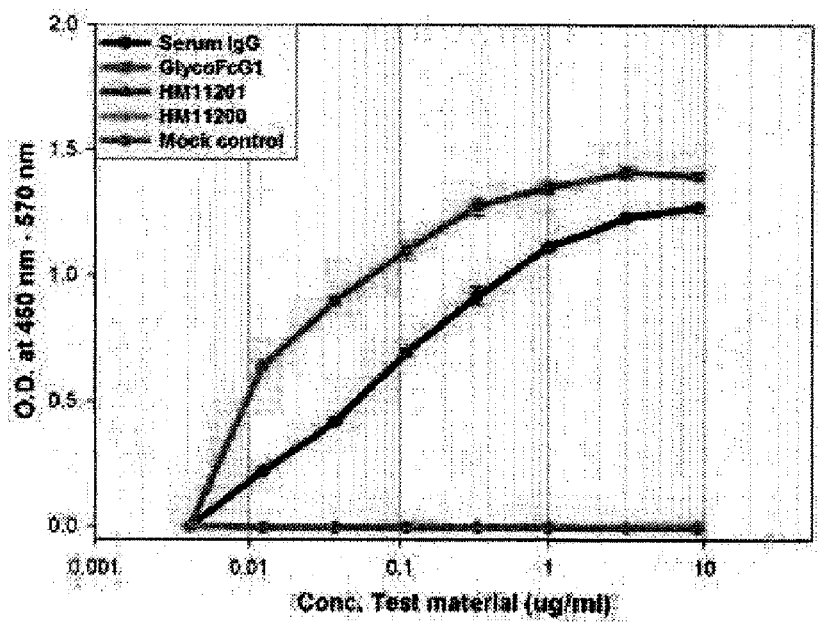
FIG. 3 shows the results of ELISA for the FcγRI binding capacity of human immunoglobulin IgG Fc region.

The FcγRI purified in Example <5-2> was diluted to a concentration of 0.75 µg/ml in PBS (pH 7.4), aliquoted onto a 96-well plate (Nunc, Maxisorp) at an amount of 100 µl per well, and incubated for 18 hours at 4° C. so that the receptor was attached to the bottom of the 96-well plate. Each well of the 96-well plate was washed three times with 300 µl of a washing buffer PBS (pH 7.4) containing 0.05% Tween-20 (Amresco, Cat. no. 0777). Then, 300 µl of PBS (pH 7.4) containing 0.1% Tween-20 and 3% BSA (bovine serum albumin, Amresco, Cat. no. 0332) was added to each well so as to prevent the undesirable attachment of other substances to the bottom of the well and incubated at 37° C. for 1 hour, after which the reaction solution was completely removed therefrom. With human serum IgG and the Fc separated by the treatment of human serum IgG with papain serving as controls, HM11200 and the HM11201 product purified in Example 2 were diluted to a concentration of 9 µg/ml in respective assay buffers, followed by repeating a 1:3 serial dilution with the assay buffer seven times. 100 µl of the dilution was placed in each well of a 96-well plate and allowed to react at 25° C. for 2 hours with shaking at a constant rate, and the wells were washed six times with a washing buffer. In order to examine whether the HM11200, the HM11201 product and the controls, all of which were anchored to the bottom of the well plate, were bound to FcγRI, a 1:100000 dilution of an HRP-conjugated goat anti-human heavy chain antibody (Chemicon, AP309P) in an assay buffer was placed at a volume of 100 µl in each well and allowed to react at 25° C. for 2 hours with shaking at a constant rate. After washing six times with a washing buffer, 100 µl of a substrate (BD bioscience, Cat. no. 555214), which was able to react with the HRP conjugated with the antibody, was placed in each well and reacted at 25° C. for 20 min. The reaction was terminated with 2N sulfuric acid and color intensity was measured with an ELISA reader (Molecular Devices, microplate reader) at 450 nm. As seen in FIG. 3, almost none of the Fc proteins produced in $E.$ $coli$ bound to FcγRI while human IgG and Fc, both glycosylated, were strongly associated with FcγRI.

<5-4> Assay for Binding to FcγRIII

With human serum IgG and the Fc separated by the treatment of human serum IgG with papain serving as controls, HM11200 and the HM11201 product purified in Example <1-2> were diluted to a concentration of 9 µg/ml in respective carbonate buffer (pH 9.0), followed by repeating a 1:3 serial dilution with the carbonate buffer seven times. 100 µl of the dilution was placed on each well of a 96-well plate and incubated at 4° C. for 18 hours so that they were attached to the bottom of the 96-well plate. Each well of the 96-well plate was washed three times with 300 µl of a washing buffer consisting of PBS (pH 7.4) containing 0.05% Tween-20 (Amresco, Cat. no. 0777). Then, 300 µl of an assay buffer consisting of PBS (pH 7.4) containing 0.1% Tween-20 and 5% non-fat dry milk (Difco, Cat. No. 232100) was added to each well to prevent the undesirable attachment of other substances onto the bottom of the well, and was incubated at 37° C. for 1 hour, followed by complete removal of the reaction solution. The FcγRIII purified in Example <4-2> was diluted to a concentration of 1 µg/ml in the assay solution. 100 µl of the dilution was placed in each well of a 96-well plate and allowed to react at 25° C. for 2 hours with shaking at a constant rate. The wells were washed six times with a washing buffer. A rabbit anti-GST antibody (Chemicon, AB3282), which was able to bind to the GST (glutathione S-transferase) of FcγRIII associated with the HM11200, the HM11201 product and the controls, was diluted 1:10000 in the assay buffer, and 100 µl of the dilution was placed in each well and allowed to react at 25° C. for 2 hours with shaking at a constant rate. Subsequently, after washing the wells six times with a washing buffer, 100 µl of a 1:7500 dilution of the antibody against the rabbit antibody in the assay buffer was placed on each well.

Figure 4:
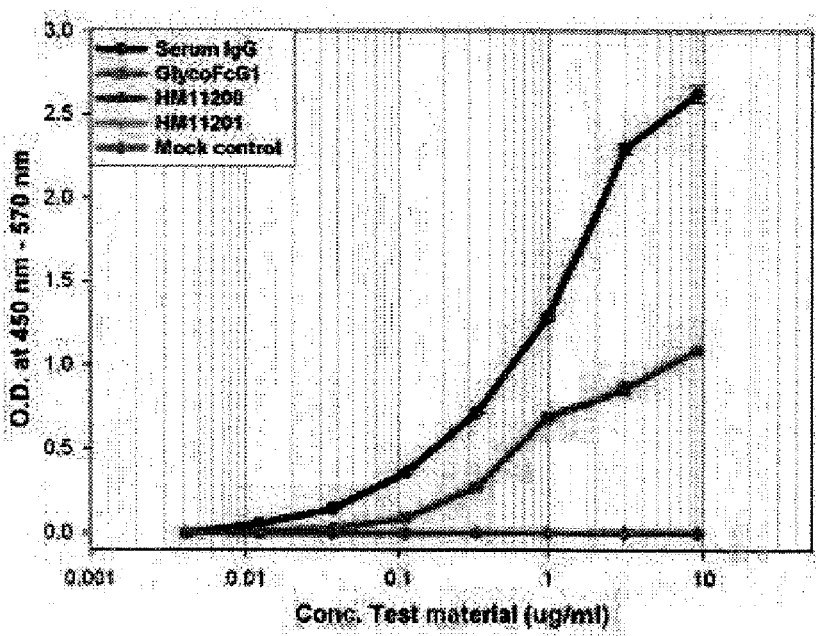
FIG. 4 shows the results of ELISA for the FcγRIII binding capacity of human immunoglobulin IgG Fc region.

Following reaction at 25° C. for 2 hours with shaking at constant rate, the 96-well plate was washed six times with a washing buffer. A substrate was added in the same manner as in Example <5-3> and color intensity was measured with an ELISA reader. As seen in FIG. 4, almost none of the FcγRIII proteins produced in $E.$ $coli$ bound to FcγRI while human IgG and Fc, both glycosylated, were strongly associated with FcγRIII.

<5-5> Assay for Binding to FcRnαβ$_2$

With human serum IgG, and the Fc separated by the treatment of human serum IgG with papain serving as controls, HM11200 and the HM11201 product purified in Example <1-2> were diluted to a concentration of 20 µg/ml in respective carbonate buffer (pH 9.0), followed by repeating a 1:3 serial dilution with the carbonate buffer seven times. 100 µl of the dilution was placed on each well of a 96-well plate and incubated at 4° C. for 18 hours so that they were attached onto the bottom of the 96-well plate. Each well of the 96-well plate was washed three times with 300 µl of a washing buffer consisting of PBS (pH 7.4) containing 0.05% Tween-20 (Amresco, Cat. no. 0777). Then, 300 µl of an assay buffer consisting of PBS (pH 7.4) containing 0.1% Tween-20 and 0.5% BSA (Amresco, Cat. No. 0332) was added to each well to prevent the undesirable attachment of other substances to the bottom of the well, and was incubated at 37° C. for 1 hour, followed by complete removal of the reaction solution. The FcRnαβ$_2$ purified in Example <5-2> was diluted to a concentration of 3 µg/ml in the assay solution. 100 µl of the dilution was placed in each well of a 96-well plate and allowed to react at 25° C. for 2 hours with shaking at a constant rate. The wells were washed six times with the washing buffer. A rabbit anti-GST antibody (Chemicon, AB3282), which was able to bind to the GST (glutathione S-transferase) of FcRnαβ$_2$ associated with the HM11200, the HM11201 product and the controls, was diluted 1:10000 in the assay buffer, and 100 µl of the dilution was placed in each well and allowed to react at 25° C. for 2 hours with shaking at a constant rate. Subsequently, after washing the wells six times with a washing buffer, 100 µl of a 1:7500 dilution of an antibody against the rabbit antibody in the assay buffer was placed in each well.

Figure 5:
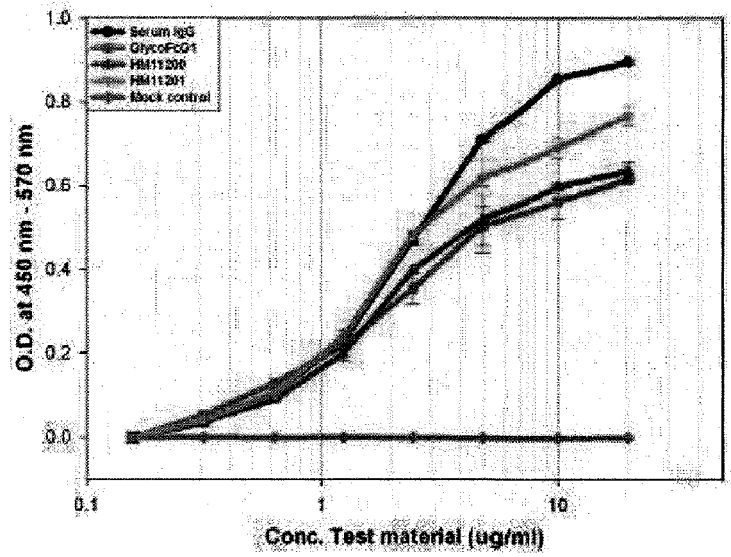
FIG. 5 shows the results of ELISA for the FcRn$\alpha\beta_2$ binding capacity of human immunoglobulin IgG Fc region.

Following reaction at 25° C. for 2 hours with shaking at a constant rate, the 96-well plate was washed six times with a washing buffer. A substrate was added in the same manner as in Example 5-2, and color intensity was measured with an ELISA reader. Like human IgG and glycosylated Fc, as seen in FIG. 5, the Fc proteins produced in $E.$ $coli$ strongly bind to FcRnαβ$_2$.

EXAMPLE 6

Preparation and Pharmacokinetic Analysis of Human EPO Conjugate

<6-1> Preparation of Human EPO

To prepare a human EPO (erythropoietin) conjugate, first, an EPO gene was amplified through RT-PCR using total RNA isolated from blood cells and cloned into a pBluscript II (Stratagen) vector, thus generating a pBlueEP vector. To transfer the cloned EPO gene into an animal cell expression vector pCMV/dhfr-(pCDNA3.1 (Invitrogen Company) containing a dhfr gene), the pBlueEP was digested with HindIII and BamHI, and the EPO gene-containing fragment thus obtained was inserted into the animal cell expression vector treated with the same restriction enzymes, thus providing pcmvEP. This expression vector carrying an EPO gene was transfected into CHO cells, a protein expression strain, using a Lipofectamine reagent (Gibco). The cells were treated with gradually increasing concentrations of MTX to 120 nM to elevate expression levels thereof. EPO was expressed at high levels, higher than 100 mg per liter.

<6-2> Preparation of Human EPO-PEG Complex

ALD-PEG-ALD (Shearwater), a 3.4-kDa polyethylene glycol having an aldehyde reactive group at both ends, was mixed with amounts of a 100 mM phosphate buffer containing the EPO prepared in <6-1> at a concentration of 5 mg/ml appropriate to form an EPO: PEG molar ratio of 1:1, 1:2.5, 1:5, 1:10 and 1:20. To this mixture, a reducing agent, sodium cyanoborohydride (NaCNBH$_3$, Sigma), was added at a final concentration of 20 mM and was allowed to react at 4° C. for 2 hrs with gentle agitation to allow PEG to selectively link to the amino terminal end of EPO. To obtain a 1:1 complex of PEG and EPO, the reaction mixture was subjected to size exclusion chromatography using a Superdex® column (Pharmacia). The EPO-PEG complex was eluted from the column using 10 mM potassium phosphate buffer (pH 6.0) as an elution buffer, and EPO not linked to PEG, unreacted PEG and dimer byproducts, where PEG was linked to two EPO molecules were removed. The purified EPO-PEG complex was concentrated to 5 mg/ml. Through this experiment, the optimal reaction molar ratio for EPO to PEG, providing the highest reactivity and generating the smallest amount of byproducts such as dimers, was found to be 1:2.5 to 1:5.

<6-3> Preparation of Conjugate of Human EPO-PEG Complex and Recombinant Immunoglobulin Fc Region The EPO-PEG complex prepared in Example <6-2> was linked to an immunoglobulin Fc region produced using the HM11201 in Example <1-3>. In detail, the immunoglobulin Fc region fragment (about 53 kDa) prepared in Example <1-3> was dissolved in 10 mM phosphate buffer and mixed with the EPO-PEG complex at an EPO-PEG complex: Fc region molar ratio of 1:1, 1:2, 1:4 and 1:8. After the phosphate buffer concentration of the reaction solution was adjusted to 100 nM, a reducing agent, $NaCNBH_3$, was added to the reaction solution at a final concentration of 20 mM and was allowed to react at 4° C. for 20 hrs with gentle agitation. Through this experiment, the optimal reaction molar ratio for EPO-PEG complex to Fc region fragment, providing the highest reactivity and generating the fewest byproducts such as dimers, was found to be 1:2.

After the coupling reaction, the reaction mixture was subjected to high-pressure liquid chromatography so as to eliminate unreacted substances and byproducts. The coupling reaction solution was desalted using a HiPrep 26/10 desalting column (Pharmacia) with 10 mM Tris buffer (pH 8.0). Then, the reaction solution was loaded onto 50 ml of a Q HP 26/10 column (Pharmacia) at a flow rate of 8 ml/min, and this column was eluted with a linear NaCl gradient of 0 M-0.2 M to obtain desired fractions. The collected fractions were again loaded onto a polyCAT 21.5×250 column equilibrated with 10 mM acetate buffer (pH 5.2) at a flow rate of 15 ml/min, and this column was eluted with a linear NaCl gradient of 0.1-0.3 M, thus providing highly pure fractions.

<6-4> Pharmacokinetic Analysis

The native EPO prepared in Example <5-1>, Aranesp (Amgen) having a greater sialic acid content so as to increase the half-life thereof, and the EPO-PEG-Fc conjugate (test group) prepared in Example <5-3> were subcutaneously injected at a dose of 100 μg/kg into five SD rats per group. After the subcutaneous injection, blood samples were collected at 0.5, 1, 2, 4, 6, 12, 24 and 48 hrs in the control groups and at 1, 12, 24, 30, 48, 72, 96, 120, 144, 168, 192, 240, 288, 336 and 384 hrs in the test groups. The blood samples were collected in 1.5 ml tubes, coagulated, and centrifuged for 10 min using an Eppendorf high-speed micro centrifugator to remove blood cells. Serum protein levels were measured by ELISA using an antibody specific to EPO.

Figure 6:
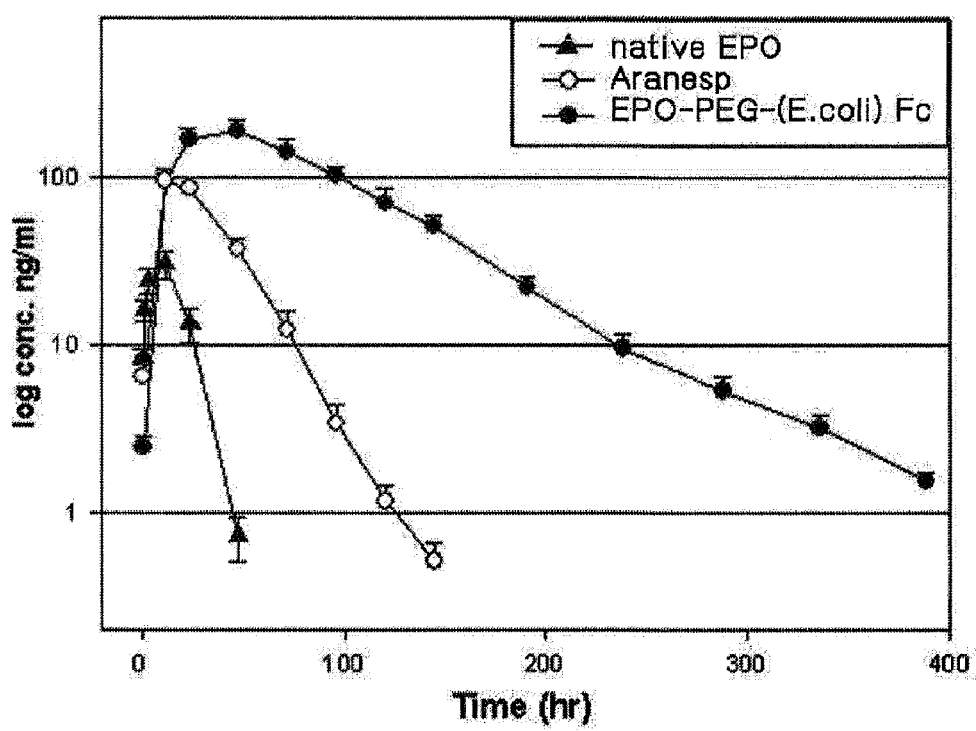
FIG. 6 shows the results of serum half lives of an EPO-PEG-Fc conjugate prepared using a human immunoglobulin IgG Fc region as a carrier.

Table 6, below, and FIG. 6 show serum half-lives of the native protein and the protein conjugate. The EPO-PEG-Fc (*E. coli*) protein conjugate, prepared using the immunoglobulin Fc region produced according to the present invention as a carrier, exhibited a much longer serum half-life than that of the native EPO. This extended half-life was found to be higher than that of Aranesp, known to be a second generation EPO having a long serum half-life.

TABLE 6

| | EPO | EPO-PEG-Fc conjugate | Aranesp |
|---|---|---|---|
| $C_{max}^1$ (ng/ml) | 30.4 | 192.8 | 96.8 |
| $T_{max}^2$ (hr) | 12.0 | 48.0 | 12.0 |
| $T_{1/2}^3$ (hr) | 6.1 | 47.0 | 16.4 |
| $AUC^4$ (ng · hr/ml) | 713 | 20436 | 4064 |
| $MRT^5$ (hr) | 15.1 | 88 | 32 |

[1]Maximal serum concentration
[2]Time taken to reach the maximal drug concentration
[3]Serum half-life of a drug
[4]Area under the serum concentration versus time curve
[5]Mean time that a drug molecule resides in the body

INDUSTRIAL APPLICABILITY

As described hitherto, the method according to the present invention allows the mass production of an immunoglobulin Fc region in an inclusion body form in *E. coli* using a recombinant immunoglobulin Fc region comprising a hinge region. When linked to a physiologically active protein, the produced immunoglobulin Fc region can be effectively used to enhance the serum half-life and physiological activity of the physiologically active protein with no risk of inducing immune responses.

The invention claimed is:

1. A method of producing an immunoglobulin Fc region free of an initial methionine residue, comprising:
   preparing a recombinant expression vector including a nucleotide sequence coding for a recombinant immunoglobulin Fc region composed of an immunoglobulin Fc region linked at the N-terminus thereof to an immunoglobulin hinge region via a peptide bond;
   transforming a prokaryotic cell with the recombinant expression vector to create a transformant;
   culturing the transformant to express the immunoglobulin Fc region as an inclusion body; and
   isolating the immunoglobulin Fc region,
   wherein the immunoglobulin hinge region has cysteine, serine or proline as an initial amino acid of the N-terminus.

2. The method according to claim 1, wherein the immunoglobulin Fc region is isolated in a monomeric or dimeric form.

3. The method according to claim 1, wherein the hinge region has two or more consecutive amino acid sequences derived from the hinge region of IgG, IgA, IgM, IgE, or IgD.

4. The method according to claim 3, wherein the hinge region has two or more consecutive amino acid sequences, each including at least one cystein residue.

5. The method according to claim 3, wherein the IgG is selected from the group consisting of IgG1, IgG2, IgG3 and IgG4.

6. The method according to claim 5, wherein the hinge region has an amino acid sequence selected from the group consisting of SEQ ID NO. 18, 19, 20, 21, 49, 51, 53, 54, 55, 56, 57, 58, 59 and 60.

7. The method according to claim 1, wherein the immunoglobulin Fc region is selected from the group consisting of Fc regions from IgG, IgA, IgM, IgE, IgD, and combinations and hybrids thereof.

8. The method according to claim 7, wherein the immunoglobulin Fc region is the Fc region of the IgG selected from the group consisting of IgG1, IgG2, IgG3, IgG4, and combinations and hybrids thereof.

9. The method according to claim 1, wherein the immunoglobulin Fc region is composed of one to four domains selected from the group consisting of CH1, CH2, CH3, CH4 and CL domains.

10. The method according to claim 1, wherein the recombinant immunoglobulin Fc region has an amino acid sequence selected from the group consisting of SEQ ID NO. 7, 9, 11, 13, 25, 29, 31, 33, 35, 37, 39, 41, 43, 45, and 47.

11. The method according to claim 1, wherein the recombinant expression vector includes a nucleotide sequence encoding an amino acid sequence selected from the group consisting of SEQ ID NO. 7, 9, 11, 13, 25, 29, 31, 33, 35, 37, 39, 41, 43, 45 and 47.

12. The method according to claim 1, wherein the prokaryotic cell is *E. coli*.

13. The method according to claim 1, wherein the transformant is transformed with a recombinant expression vector including a nucleotide sequence encoding an amino acid sequence selected from the group consisting of SEQ ID NO. 7, 9, 11, 13, 25, 29, 31, 33, 35, 37, 39, 41, 43, 45 and 47.

14. A monomeric or dimeric immunoglobulin Fc region free of initial methionine residues, prepared by the method of claim 1.

15. The method according to claim 13, wherein the transformant is selected from the group consisting of the transformants deposited under Accession Nos. KCCM-10659P, KCCM-10660P, KCCM-10665P and KCCM-10666P.

* * * * *

UNITED STATES PATENT AND TRADEMARK OFFICE
CERTIFICATE OF CORRECTION

PATENT NO. : 7,968,316 B2
APPLICATION NO. : 12/063379
DATED : June 28, 2011
INVENTOR(S) : Sung Youb Jung et al.

It is certified that error appears in the above-identified patent and that said Letters Patent is hereby corrected as shown below:

In The Claims

Claim 1 should read:

1. A method of producing a recombinant immunoglobulin Fc region free of an initial methionine residue, comprising:

preparing a recombinant expression vector including a nucleotide sequence coding for a recombinant immunoglobulin Fc region composed of an immunoglobulin Fc region linked at the N-terminus thereof to an immunoglobulin hinge region via a peptide bond;

transforming a prokaryotic cell with the recombinant expression vector to create a transformant;

culturing the transformant to express the recombinant immunoglobulin Fc region as an inclusion body; and isolating the recombinant immunoglobulin Fc region, wherein the immunoglobulin hinge region has cysteine, serine or proline as an initial amino acid of the N-terminus.

Claim 2 should read:

2. The method according to claim 1, wherein the recombinant immunoglobulin Fc region is isolated in a monomeric or dimeric form.

Signed and Sealed this
Twenty-second Day of March, 2016

Michelle K. Lee
*Director of the United States Patent and Trademark Office*